United States Patent [19]
Zalewski et al.

[11] Patent Number: 6,159,946
[45] Date of Patent: Dec. 12, 2000

[54] ANTISENSE INHIBITION OF C-MYC TO MODULATE THE PROLIFERATION OF SMOOTH MUSCLE CELLS

[75] Inventors: Andrew Zalewski, Elkins Park; Yi Shi, Cheltenham, both of Pa.

[73] Assignee: Thomas Jefferson University, Philadelphia, Pa.

[21] Appl. No.: 08/481,341

[22] PCT Filed: Jan. 7, 1994

[86] PCT No.: PCT/US94/00265

§ 371 Date: Jul. 7, 1995

§ 102(e) Date: Jul. 7, 1995

[87] PCT Pub. No.: WO94/16189

PCT Pub. Date: Jul. 21, 1994

Related U.S. Application Data

[63] Continuation-in-part of application No. 08/004,799, Jan. 7, 1993, abandoned.

[51] Int. Cl.$^7$ .......................... C07H 21/04; A61K 48/00
[52] U.S. Cl. ................................ 514/44; 435/6; 435/375; 435/455; 536/23.1; 536/24.1; 536/24.5
[58] Field of Search ............................... 435/91.1, 6, 375, 435/455; 514/44; 536/23.1, 24.1, 24.3, 24.31, 24.5; 935/62

[56] References Cited

U.S. PATENT DOCUMENTS

| | | |
|---|---|---|
| 5,245,022 | 9/1993 | Weis et al. . |
| 5,264,423 | 11/1993 | Cohen et al. . |
| 5,276,019 | 1/1994 | Cohen et al. . |
| 5,286,717 | 2/1994 | Cohen et al. . |
| 5,593,974 | 1/1997 | Rosenberg et al. ........................ 514/44 |
| 5,756,476 | 5/1998 | Epstein et al. ............................ 514/44 |

FOREIGN PATENT DOCUMENTS

| | | |
|---|---|---|
| WO 90/03189 | 4/1990 | WIPO . |
| WO 92/05305 | 1/1993 | WIPO . |
| WO 93/08845 | 5/1993 | WIPO . |
| WO 94/15645 | 7/1994 | WIPO . |
| WO 94/15646 A1 | 7/1994 | WIPO . |
| WO 94/15943 | 7/1994 | WIPO . |
| WO 94/26888 | 11/1994 | WIPO . |
| WO 94/28721 | 12/1994 | WIPO . |
| WO 95/10305 A1 | 4/1995 | WIPO . |

OTHER PUBLICATIONS

Bennet "Antisense Research", Science vol. 271, p. 434, 1996.
Milligan et al "Current Concepts in Antisense Drug Design", J. Medicinal Chem. vol. 36 (4) pp. 1923–1937, 1993.
Westerman et al "Inhibition of expression of SV40 large T–antigen by antisense oligodoxypribonucleotides", Biomed Biochem Acta vol. 48(1):85–93, 1989.
Burgess et al. "Me Antiproliferative activity of c–myb and c–myc Antisense olgonucleotides in Smooth Muscles is caused by a nonantisense Mechanism" PNAS vol. 92: 4051–4055 1995.
Weiss et al "Antisense ", Science News vol. 139, 108–109, 1991.
Sten et al "Antisense Oligonucleotides as therapeutic Agents–Is the Bullet Really Magical?" Science vol. 261:10–1012, 1993.
Wague et al, "Gene Inhibitor using Antisense oligotooxynucleotides" Nature vol. 372:333–335, 1994.
Gura "Antisense Has Growing Pains" Science vol. 270:575–577, 1995.
Stull et al "Antigen, Ribozyme and Metoner Nucleic Acid Drugs: Progress & Prospects." Pharmaceutical Research vol. 12(4):465–483, 1995.
Wu–Pong "Oligonucleotides: Opportunities for Drug Therapy & Research" Pharm. Tech. vol. 18:102–114, 1994.
Miller et al "Gene Transfer & Nucleic Acid Techniques" Parisitology Today, vol. 10(3):92–97, 1994.
Rojanasakul "Antisense oligonucleotides therapuetics:Drug Delivery and targeting", Advanced Drug Delivery Reviews, vol. 18:115–131, 1996.
Lambert et al. "The Perforated Balloon Catheter: Assesment and Minimization of Arterial Trauma" J. Am. Coll. Cardiol. vol. 19 Suppl A:107A, Apr. 1992.
Watson et al., "Inhibition of cell adhesion to plastic substratum by phosphorothioate oligonucleotide", Experimental Cell Research, 202(2) 391–7 XP000644735 (1992 Oct.).
Wilensky et al., "Methods and devices for local drug delivery in coronary and peripheral arteries", Trends In Cardiovascular Medicine, vol. 3, 163–70, XP000644584 (Sep. 1993–Oct. 1993).
Shi, et al., "Regulation of extracellular matrix synthesis by antisense oligomers targeting the c–myc", Circulation 90(4) (Part 2) Abstract 2767, XP000644592 (Oct. 1994).
Abe et al. "Biochem and Biophysical Research Communications", 198:1:16–24, Jan. 14, 1994.
Agrawal, "Pharmacokinetics, biodistribution, and stability of ligodeoxynucleotide phosphorothioates in mice", Proc. Natl. Acad. Sci. USA vol. 88, pp. 7585–7599, Sep. 1991.
Agrawal, et al., "Antisense Oligonucleotide Based Therapeutic Approach: From Laboratory to Clinical Trials", Antisense Therapy: Efficacy and Delivery of Antisense & Ribozine Oligonucleotide (Feb. 23–25, 1995 London).
Ang et al., "Collagen synthesis by cultured rabbit aortic smooth–muscle cells", Biochem 265:461–469 (1990).
Barinaga M., "Gene Therapy for Clogged Arteries Passes Test in Pigs" Science 265:738, Aug. 5, 1994.
Bauters et al., "Proto–oncogene expression in rabbit aorta after wall injury First Marker of the cellular process leading to restenosis after angioplasty" European Heart Journal, 13:556–559 (1992).

(List continued on next page.)

Primary Examiner—John S. Brusca
Assistant Examiner—Sean McGarry
Attorney, Agent, or Firm—Seidel, Gonda, Lavorgna & Monaco, PC

[57] ABSTRACT

The present invention provides antisense therapies useful for modulating smooth muscle cell proliferation. Methods of treating and preventing restenosis are also provided.

12 Claims, 9 Drawing Sheets

OTHER PUBLICATIONS

Bayever, et al., "Oligonucleotides In The Treatment of Leukemia" *Hematological Oncology*, vol. 12:9–14, (1994).

Beldekas et al., "Cell Density and Estradiol Modulation of Procollagen Type III in Cultured Calf Smooth Muscle Cells*" *The Journal of Biological Chemistry*, 257:20:12252–12256, Oct. 25, 1982.

Biro et al., "Inhibitory Effects of Antisense Oligonucleotides targeting c–myc mRNA on Smooth Muscle Cell Proliferation and Migration", *Proc. Natl. Acad. Sci.* 90:654–658 (1993).

Brown et al., "Expression of the c–myb Proto–Oncogene in Bovine Vascular Smooth Muscle Cells*" *The Journal of Biological Chemistry*, 267:7:4625–4630, Mar. 5, 1992.

Castellot, "Effect of Heparin on Vascular Smooth Muscle Cells . . . ", *Journal of Cellular Physiology*, 124:21–28 (1985).

Chang and Sonenshein, "Increased Collagen Gene Expression in Vascular Smooth Muscle Cells Cultured in Serum or Isoleucine Deprived Medium", *Matrix*, vol. 11:242:251 (1991).

Collins et al., "c–myc Antisense Oligonucleotides Inhibit the Colony–Forming Capacity of Colo 320 Colonic Carcinoma Cells", *Journal of Clinical Investigation*, vol. 89:1523–1527, (1992).

Crooke, "Therapeutic Applications of Oligonucleotides", *Annu. Rev. Pharmacol. Toxicol*, 32:329–376, (1992).

de Fabritiis, et al., "In vitro Purging with BCR–BRL Antisense Oligonucleotide does not Prevent Haematologic Resonstitution After Autologous Bone Marrow Transplantation,"*Leukemia*, 9(4):662–664, (1995).

Dreher et al., "Expression of antisense transcripts encoding an extracellular matrix protein by stably tranfected vascular smooth muscle cells" *Eur. J. Cell Biol.* 54 (1991) pp. 1–9.

Ebbecke et al., "Antiproliferative effects of a c–myc antisense oligonucleotide on human arterial smooth muscle cells" *Basic Res Cariol*, 87: 585–591 (1992).

Ebbecke et al., "Inhibition of Human Arterial Smooth Muscle Cell Proliferation by a c–myc Antisense Oligonucleotide", *Abstract, XIIIth Congress of the European Society of Cardiology* 18–22 Aug. 1991, Amsterdam, The Netherlands (No. 677).

Ebecke et al., "In vitro Assessment of Polyactides as Slow Release Drug Carriers", *Supplement to Circulation*, vol. 84(4), Abstract No. 0285, (1991).

Edelman et al., "Perivascular and Intravenous Administration of Basic Fibroblast Growth Factor: Vascular and Solid Organ Deposition", *Proc. Natl. Acad. Sci.*, vol. 90:1513–1517, (1993).

Edelman et al., "Effect of Controlled Adventitial Heparin Delivery on Smooth Muscle Cell Proliferation Following Endothelial Injury", *Proc. Natl. Acad. Sci.*, vol. 87:3773–3777, (1990).

Edelman et al., "c–myc in Vasculoproliferative Disease", *Circulation Research*, vol. 76(2): 176–182, (1995).

Epstein et al., "Inhibition of Cell Proliferation using Antisense Oligonucleotides. (Use of c–myc Antisense to Inhibit Cell Proliferation Associated with Restenosis)" *NTIS Publication* PB93–100576 (Jan. 1, 1993), pp. 1–38.

Fard et al., "Mechanisms of Neointimal Reduction after Transcatheter Delivery of C–myc Antisense Oligomers" *Circulation*, 90:I–191, abstract No. 1022, Nov. 1994.

Farquharson et al., "Immunolocalization of Collagen Types I and III in the Arterial Wall of the Rat", *Histochemical Journal*, 21(3):172–178 (1989).

Fernandez–Ortiz et al., "A New Approach for Local Intravascular Drug Delivery", *Circulation*, vol. 89(4):1518–1522, (1994).

Fox et al., "Fish Oils Inhibit Endothelial Cell Production of Platelet–Derived Growth Factor–Like Protein" *Science*, 241:453–456 (1988).

Gabbiani et al., "Actin Expression in Smooth Muscle Cells of Rat Aortic Intimal Thickening, Human Atheromatous Plaque, and Cultured Rat Aortic Media" *J. Clin Invest.*, 73:148–152, Jan. 1984.

Gazin et al., "Nucleotide sequence of the human c–myc locus: provocative open reading frame within the first exon" *The EMBO Journal*, 3:2:383–387, 1984.

Hanke et al., "Prolonged Proliferative Response of Smooth Muscle Cells after Experimental Intravascular Stenting: A Stent Wire Related Phenomenon" *Abstract, Supplement to Circulation*, 86:4:I–186, Oct. 1992 (0742).

Hiija, et al., Biologic and Therapeutic Significance of MYB Expression in Human Melanona, *Proc. Natl. Acad. Sci.*, vol. 91:4499–4503, (1994).

Holmes et al., "restenosis," from PTCA (Percutaneous Transluminal Coronary Angioplasty), Chapter 12:161–175, (Viliestra & Holmes) (1990).

Holt et al. An Oligomer Complementary to c–myc mRNA Inhibits Proliferation of HL–60 Promyelocytic Cells and Induces Differentiation. *Molecular and Cellular Biology* 8:963–973 (1988).

Hutchinson et al., "Inhibition of Human Vascular Smooth Muscle Cell Proliferation Using c–myc Antisense Oligonucleotides" *Abstract, Supplement to Circulation*, 86:4:I–226, Oct. 1992 (0898).

Hutchinson et al., "Inhibition of Porcine Vascular Smooth Muscle Cell Proliferation Using c–myc Antisense Oligonucleotides" *Abstract, JACC*, 21:2:327A Feb. 1993 (786–5).

Iversen, "In vivo Studies with Phosphorothioate Oligonucleotides: Pharmacokinetics Prologue", *Anti–Cancer Drug Design*, 6:531–538, (1991).

Karas et al. "Coronary Intimal Proliferation After Balloon Injury and Stenting in Swine: An Animal Model of Restenosis" *JACC*, 20:2:467–74, Aug. 1992.

Kindy et al., "Regulation of Oncogene Expression in Cultured Aortic Smooth Muscle Cells." *J. Biol Chem.* 261:12865–12868 (1986).

Kovalik et al., "Correction of Central Venous Stenoses: Use of Angioplasty and Vascular Wallstents", *Kidney International*, 45:1177–1181, (1994).

Langer et al., "Controlled Release and Magnetically Modulated Release Systems for Macromolecules", *Methods in Enzymology*, 112:399–422 (1985).

Libby et al., "A Cascade Model for Restenosis", Supplemental III Circulation, 86(6):III47–III52, (1992).

Majesky et al., "Production of Transforming Growth Factor $\beta_1$ during Repair of Arterial Injury" *J. Clin Invest.*, 88:904–910, Sep. 1991.

Majesky et al., "Rat Carotid Neointimal Smooth Muscle Cells Reexpress a Developmentally Regulated mRNA Phenotype During Repair of Arterial Injury" *Circulation Research*, 71:4:759–768, Oct. 1992.

Marcu et al., "myc Function and Regulation", *Ann. Rev. Biochem*, 61:809–860 (1992).

McCullagh et al., "Collagen Characterisation and Cell Transformation in Human Atherosclerosis", *Nature*, 258:73–75 (1975).

McGraw et al., "Sequence–Dependent Oligonucleotide–Target Duplex Stabilities: Rules from Empirical Studies with a Set of Twenty–Mers" *BioTechniques*, 8:6:674–678 (1990).

Miano et al. "Early Proto–Oncogene Expression in Rat Aortic Smooth Muscle Cells Following Enothelial Removal", *Am. J. Pathology*, 137:4:61–765 (1990).

Mirabelli et al., "In vitro and in vivo pharmacologic activities of antisense oligonucleotides" *Anti–Cancer Drug Design* 6:647–661, Dec. 1991.

Miyashi et al., "Distribution of the Collagen Binding Heat–shock Protein in Chicken Tissues" *The Journal of Histochemistry and Cytochemistry*, 40:7:1021–1029, 1992.

Morishita et al., "Single intraluminal delivery of antisense cdc2 kinase and proliferating–cell nuclear antigen oligonucleotides results in chronic inhibition of neointimal hyperplasia" *Proc. Natl. Acad. Sci.*, 90:8474–8478 (1993).

Muller et al., "Experimental Models of Coronary Artery Restenosis" *JACC*, 19:2:418–32, Feb. 1992.

Nabel et al., "Direct Gene Transfer with DNA–Liposome Complexes in Melanona: Expression, Biologic Activity, and Lack of Toxicity in Humans", *Proc. Natl. Acad. Sci.*, vol. 90:11307–11311, (1993).

O'Brien et al., "Proliferation in Primary and Restenotic Coronary Atherectomy Tissue" *Circulation Research*, 73:2:223–231, Aug. 1993.

O'Brien et al., "Inhibition of Cell Proliferation by C–myc Antisense Oligomers Following Surgical Revascularization" *Circulation* 92:8:1297, abstract No. 1414 (Nov. 1995).

Offensperger et al., "In vivo Inhibition of Duck Hepatitis B Virus Replication and Gene Expression by Phosphorothioate Modified Antisense Oligodeoxynucleotides", *The EMBO Journal*, 12(3) 1257–1262, (1993).

Ohno et al., "Gene Therapy for Vascular Smooth Muscle Cell Proliferation After Artierial Injury" *Science*, 265:781–784, Aug. 5, 1994.

Pickering et al., "Proliferative Activity in Peripheral and Coronary Atherosclerotic Plaque among Patients Undergoing Percutaneous Revascularization" *J. Clin. Invest.* 91:1469–1480, Apr. 1993.

Pickering et al., "Collagen Elaboration Following Balloon Angioplasty—Evidence for Rapid Expression and Deposition" *Abstract, JACC*, Feb. 1994:1A–484A, p. 235A (No. 906–37).

Plante et al., "Porous Balloon Catheters for Local Delivery: Assessment of Vascular Damage in a Rabbit Iliac Angioplasty Model" *JACC*, 24:3:820–824, Sep. 1994.

Powell et al., "Inhibitors of Angiotensin–Converting Enzyme Prevent Myointimal Proliferation After Vascular Injury", *Science*, 245:186–188, (1989).

Ratajczak et al., "In vivo treatment of heman leukemia in a scid mouse model with c–myb antisense oligodeoxynucleotides", *Proc. Natl. Acad. Sci.*, 89: 11823–11827 (1992).

Ratajczak et al., "Oligonucleotide Therapeutics for Human Leukemia, Antisense Therapy", *Efficacy and Delivery of Antisense & Ribozyme Oligonucleotides*, (Presented Feb. 23–24, 1995, London).

Rhine et al., "Polymers for Sustained Macromolecule Release: Procedures to Fabricate Reproducible Delivery Systems and Control Release Kinetics", *Journal of Pharmaceutical Sciences*, 69(3):265–270, (1980).

Rhodes, "The Blood Vessell", *Chapter 20 in Weiss et al. Editors, Collagen in Health and Disease,* (Churchill Livingstone, Edinburgh, 1981).

Riessen et al., "Prospects for Site–Specific Delivery of Pharmacologic and Molecular Therapies" *JACC*, 23:5:1234–1244, Apr. 1994.

Ross et al., "I. Cell Constitution and Characteristics of Advanced Lesions of the Superficial Femoral Artery" *Human Atherosclerosis*, 114:1:79–93. (Jan. 1984).

Ross, "The Pathogenesis of Atherosclerosis: a Prespective for the 1990s", *Nature,* 362:801–809 (1993).

Rothenberg et al., "Oligodeoxynucleotides as Anti–Sense Inhibitors of Gene Expression: Therapeutic Implications", *Commentary*, 81(20):1539–1544, (1989).

Schwartz et al., "Restenosis After Balloon Angioplasty" *Circulation,* 82:6:2190–2200, Dec. 1990.

Shi et al., "Gene Transfer Into Coronary Vasculature Using Transcatheter Delivery" *Abstract, The Faseb Journal,* 7:4:A562, Feb. 23, 1993 (3261).

Shi et al., "Maximizing Gene Transfer Into Vascular Smooth Muscle Cells" *Abstract, JACC,* 21:2:209A, Feb. 1993 (900–37).

Shi et al., "Transcatheter Delivery of c–myc Antisense Oligomers Reduces Neointimal Formation in a Porcine Model of Coronary Artery Balloon Injury" *Circulation,* 90:2:944–950, Aug. 1994.

Shi et al., "Downregulation of c–myc Expression by Antisense Oligonucleotides Inhibits Proliferation of Human Smooth Muscle Cells" *Circulation,* 88:3:1190–1195, Sep. 1993.

Shi et al., "Inhibition of Type I Collagen Synthesis in Vascular Smooth Muscle Cells by c–myc Antisense Oligomers", *Circulation,* 90(4) (Part 2): Nos. 0787 & 2767, (1994).

Shi et al., "Safety and Efficacy of Transcatheter Delivery of C–myc Antisense Oligomers in the Coronary Vasculature" *Circulation* 90:I–393, abstract No. 2110 (Nov. 1994).

Shi et al., "C–myc Antisense Oligomers Reduce Neointima Formation in Porcine Coronary Arteries" *Journal of the American College of Cardiology* Special issue, p. 395A, abstract No. 798–5 (Mar. 1994).

Simons et al., "Antisense Nonmuscle Myosin Heavy Chain and c–myb Oligonucleotides Suppress Smooth Muscle Cell Proliferation in Vitro", *Circulation Research,* 70(4):835–843, (1992).

Simons et al., "Antisense c–myb Oligonucleotides Inhibit Intimal Arterial Smooth Muscle Cell Accumulation In Vivo", *Nature,* 359:67–70 (1992).

Simons et al., "Antisense Proliferating Cell Nuclear Antigen Oligonucleotides Inhibit Intimal Hyperplasia in a Rat Carotid Artery Injury Model" *J. Clin. Invest.* 93:2351–2356, Jun. 1994.

Skorski, et al., "Suppression of Philadelphia Leukemia Cell Growth in Mice by BCR–ABL Antisense Oligodeoxynucleotide", *Proc. Natl. Acad. Sci.*, vol. 91:4504–4508. (May 1994).

Snoeckx et al., "Expression and cellular distribution of heat–shock and nuclear oncogene proteins in rat hearts" *The American Physiologcal Society,* H1443–H1451, 1991.

Speir et al., "A Strategy for Employing Antisense Oligonucleotides in Inhibit Smooth Muscle Cell Proliferation; Cloning and Sequencing Some Relevant Genes and Preliminary Results of Antisense ODNs Targeted to c–myc and PCNA" *NIH Research Festival Poster,* Sep. 23–24, 1991.

Speir et al., "Inhibition of Smooth Muscle Cell Prolifereation by an Antisense Oligodeoxynucleotide Targeting the Messenger RNA Encoding Proliferating Cell Nuclear Antigen", *Circulation*, 86(2):538–547, (1992).

Stein et al., "Antisense Oligonucleotides as Therapeutic Agents–Is the Bullet Really Magical?", *Science*, 261:1004–1012, (1993).

Stepp et al., "Complex Regulation of Collagen Gene Expression in Cultured Bovine Aortic Smooth Muscle Cells" *The Journal of Biological Chemistry*, 261:14:6542–6547, May 15, 1986.

Thompson et al., "Levels of c–myc oncogene mRNA are invariant throughout the cell cycle" *Nature*, 314:363–366, Mar. 28, 1985.

Uhlman and Peyman, "Antisense Oligonucleotides: a New Therapeutic Principle", *Chemical Reviews* 90:543–584 (1990).

Van der Rest et al., "Collagen Family of Proteins", *FASEB J.* 5:2814–2823 (1991).

Villa et al., "Effects of Antisense c–myb Oligonucleotides on Vascular Smooth Muscle Cell Proliferation and Response to Vessel Wall Injury", *Circularation Research*, 76(4):505–513, (1995).

Vliestra et al., Chapter 9 "Objective Assessment of Results, Chapter 12 Restenosis", *PTCA (Percutaneous Transluminal Coronary Angioplasty)*, (Davis Company, Philadelphia, 1987), pp. 105–126.

Walker et al., "Producation of Platelet–Derived Growth Factor–Like Molecules by Cultured Arterial Smooth Muscle Cells Accompanies Proliferation After Arterial Injury", *Proc. Natl. Acad. Sci.*, 83:7311–7315, (1986).

Weiss, "Upping the Antisense Ante", *Science News*, pp. 108–109 (Feb. 16, 1991).

Wetmur, "DNA probes: Applications of the principles of nucleic acid hybridization", *Critical Reviews in Biochemistry and Molecular Biology*, 26: 227–259 (1991).

Whitesell et al., "Stability, Clearance, and Disposition of Intraventricularly Administered Oligodeoxynucleotides: Implications for Therapeutic Application Within the Central Nervous System", *Proc. Natl. Acad. Sci.*, 90:4665–4669, (1993).

Wickstrom et al., "Human Promyelocytic Leukemia HL–60 Cell Proliferation and c–myc Protein Expression are Inhibited by an Antisense", *Proc. Natl. Acad. Sci.*, 85:1028–1032 (1988).

Wickstrom et al., "Antisense DNA Methylphosphonate Inhibition of c–myc Gene Expression in Trangenic Mice" *Abstract, The Faseb Journal,* 5:5:A1433, Mar. 15, 1991 (No. 6218).

Windsor et al., "Smooth Muscle Proliferation During Neointimal Development After PTCA in Swine: Identification of Site and Sequence Using Proliferating Cell Nuclear Antigen Staining" *Abstract, JACC*, Feb. 1994:1A–484A, p. 235A.

Wolinsky et al., "Use of a Perforated Balloon Catheter to Deliver Concentrated Heparin Into the Wall of the Normal Canine Artery" *JACC*, 15:5:475–81, Feb. 1990 (No. 900–35).

Woolf et al., "Specificity of Antisense Oligonucleotides in vivo", *Proc. Natl. Acad. Sci.*, 89:7305–7309, (1992).

Vu and Hirschbein, "Internucleotide Phosphite Sulfurization With Tetraethylthiuram Disulfide. Phosphorothioate Oligonucleotide Synthesis Via Phosphoramidite Chemistry" *Tetrahedron Lett.*, 32:3005–3008 (1991).

Zamecnik et al., "Inhibition of Rous Sarcoma Virus Replicationa nd Cell Transformation by a Specific Oligodeoxynucleotide", *Proc. Natl. Acad. Sci.*, 75(1):280–284, (1978).

Zeymer et al., "Proliferating Cell Nuclear Antigen Immunohistochemistry in Rat Aorta After Balloon Denudation" *PCNA Immunohistochemistry in Rat Aorta, AIP,* Sep. 1992, 141:3:685–690.

Zon, "Oligonucleotide Analogues as Potential Chemotherapeutic Agents", *Pharmaceutical Research*, 5(9):539–549, (1988).

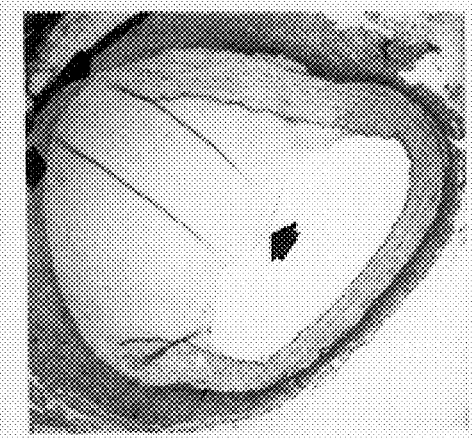
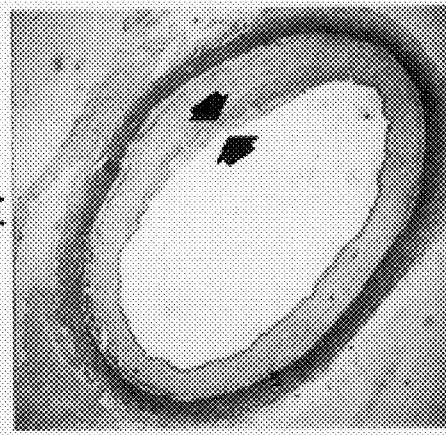
FIG. 9A  FIG. 9B
FIG. 10A  FIG. 10B
SENSE
ANTISENSE
MILD INJURY
SEVERE INJURY

ANTISENSE INHIBITION OF C-MYC TO MODULATE THE PROLIFERATION OF SMOOTH MUSCLE CELLS

CROSS REFERENCE TO RELATED APPLICATIONS

This is a continuation-in-part of application Ser. No. 08/004,799, filed Jan. 7, 1993, now abandoned.

FIELD OF THE INVENTION

This invention is directed to the modulation of smooth muscle cell proliferation by antisense therapies directed against the c-myc proto-oncogene.

BACKGROUND OF THE INVENTION

Coronary angioplasty results in successful nonsurgical revascularization in more than 90% of patients. More than 300,000 coronary angioplasty procedures were performed in the United States in 1990. However, the major limitation of coronary angioplasty is a 30–40% restenosis rate which occurs in the first six months following the procedure.

Vascular smooth muscle cells (SMC) have been identified as playing an important role in the development of atherosclerosis and restenosis following coronary angioplasty. Their presence has been confirmed in both types of lesions, and is due primarily to a change from a contractile to a synthetic phenotype of SMCs. This remarkable characteristic is associated with SMC proliferation, migration from media to intima, and the synthesis of extracellular matrix, all of which results in neointimal formation (narrowing of the artery). In contrast to atherosclerosis, where this process is extended over several decades, vascular restenosis represents an acute response to balloon injury culminating in a significant renarrowing by neointimal formation of an initially patent vessel in the course of a few months. Hence, it has become apparent that the inhibition of SMC growth is necessary to control the restenosis process.

Intensive experimental and clinical investigation for the prevention of restenosis has been conducted over the past decade. Several interventions, such as anti-platelet, anti-coagulation, anti-inflammatory and vasodilator therapies have shown favorable reduction in the severity of neointimal proliferation following experimental balloon injury. Powell et al., *Science* 1989, 245, 186–188; Castellot, J. et al., *J. Cell Physiol.* 1985, 124, 21–38; Fox et al., *Science* 1988, 241, 453–456.

Recently, attempts have also been made to apply new mechanical devices to limit restenosis (e.g., stent, atherectomy, laser, rotablator, etc.). However, preliminary data showed a limited role of these interventions because while mechanical interventions improve the primary result of coronary angioplasty, the mechanical techniques extend vessel wall injury related to the procedure and are therefore unable to reduce SMC proliferation and the restenosis rate. Furthermore mechanical interventions can be applied only to a small group of patients with optimal coronary anatomy.

Application of antimitogenic therapy has also been suggested for prevention of restenosis. For example, concentrated heparin has been tested as an antiproliferative agent to control the problem of restenosis after angioplasty. Wolinsky and Thung, *JACC* 1990, 15(2), 475–481. γ-interferon has been identified as another potentially useful therapeutic for treatment of restenosis. WO 90/03189 issued Apr. 5, 1990. However the dose of antiproliferative agents given by systemic administration is likely not high enough to achieve the desired effect. Therefore, agents which have been tested are not powerful enough to show a beneficial effect in more complex clinical situations.

Recent advances in cellular and molecular biology have provided insight into the molecular mechanisms of SMC proliferation which is due to the transduction of signals from the extracellular environment (e.g., growth factors) to the cell nucleus. Several genes become transiently activated during phenotypic modulation of SMCs (Gabbiani et al., *J Clin Invest* 1984, 73, 148–152; Walker et al., *Proc Natl Acad Sci USA* 1986, 83, 7311–7315; Miano et al., *Am J Pathol* 1990, 137, 761–765; Majesky et al., *Circulation Research* 1992, 71, 759–768). These findings have stimulated interest in defining the role of abnormal gene expression in SMC growth and in selecting potential therapeutic targets for molecular-based approaches for acquired cardiovascular disorders such as vascular restenosis. Recently, Speir and Epstein, *Circulation* 1992, 86, 538–547, showed the growth inhibition of rat smooth muscle cells using high concentrations of antisense oligonucleotide complementary to proliferating cell nuclear antigen mRNA.

Nuclear proto-oncogenes are highly conserved phosphoproteins tightly linked to cellular proliferation. The transient increase in nuclear proto-oncogene (s) mRNA following mitogenic stimulation has been shown as the cell enters the G1 phase and appears to be necessary for the G1-to-S phase transition. Studies in cultured SMCs have demonstrated that c-fos, c-myc, and c-myb proto-oncogenes are activated shortly after various mitogenic stimuli (Kindy et al., *J Biol Chem* 1986, 261, 12865–12868; Brown et al., *J Biol Chem* 1992, 267, 4625–4630). Proto-oncogene expression has also been induced in the vessel wall following balloon denudation in a pattern similar to in vitro studies (Miano et al., *Am J Pathol* 1990, 137, 761–765). The above observations and the redundancy of signal transduction pathways have raised the possibility that nuclear proto-oncogene activation is a final common pathway onto which many diverse mitogenic signals converge, making it a potential therapeutic target. Collins et al. *J. Clin. Invest.* 1992, 89, 1523–1527 found that antisense oligonucleotides complementary to c-myc inhibited the colony formation of colonic carcinoma cells. Other groups have focused on the proto-oncogene, c-myb and have found that inhibition of c-myb inhibits the proliferation of smooth muscle cells. Recently, Simon and Rosenberg, *Circulation Research* 1992, 70, 835–843 showed the growth-inhibitory effect of c-myb antisense oligonucleotides in rat smooth muscle cells.

Antisense technology is emerging as an effective means of lowering the levels of a specific gene product. It is based on the findings that these "antisense" sequences hybridize a gene or associated target polynucleotide, to form a stable duplex or triplex, based upon Watson-Crick or Hoogsteen binding, respectively. The specifically bound antisense compound then either renders the respective targets more susceptible to enzymatic degradation, blocks translation or processing, or otherwise blocks or inhibits the funciton of a target polynucleotide. Where the target polynucleotide is RNA, the antisense molecule hybridizes to specific RNA transcripts disrupting normal RNA processing, stability, and translation, thereby preventing the expression of a targeted gene. Administration of antisense oligonucleotides or transfer of expression constructs capable of producing intracellular antisense sequences complementary to the mRNA of interest have been shown to block the translation of specific genes in vitro and in vivo. For example, Holt et al., *Mol. Cell. Biol.* 1988, 8, 963–973, focusing on c-myc, found the formation of an intra-cellular duplex with target mRNA and a selective decrease of c-myc protein in human promyelocytic leukemia HL-60 cells.

Methods of modulating the proliferation of smooth muscle cells associated with restenosis in any vascular bed is greatly desired. Such method should be applicable to patients having a broad range of vascular disorders including coronary and peripheral stenoses (i.e., blockages). Further, the method should have high efficacy. Such methods are provided by the present invention.

SUMMARY OF THE INVENTION

According to the present invention, smooth muscle cells are contacted with an antisense oligonucleotide specific for c-myc to modulate proliferation of those cells.

In accordance with one preferred embodiment of the present invention is provided a method of modulating proliferation of smooth muscle cells comprising contacting smooth muscle cells with an oligonucleotide complementary to a region of mRNA encoding c-myc.

In accordance with a further preferred embodiment of the present invention is provided a method of treating a patient suffering from restenosis comprising administering to said patient a therapeutically effective amount of an oligonucleotide complementary to a region of mRNA encoding c-myc.

In a still further preferred embodiment of the present invention is provided a method of preventing vascular restenosis in a patient predisposed to restenosis comprising administering to said patient a therapeutically effective amount of an oligonucleotide complementary to a region of mRNA encoding c-myc.

BRIEF DESCRIPTION OF THE FIGURES

FIGS. 9A and 9B are photographs of a cross-section of a coronary artery of a pig one month following angioplasty. C-myc sense oligomer (SEQ ID NO:2) was given by intramural injection (2 ml under 4 atm over 27 seconds) immediately following angioplasty. Significant neointimal thickness is noted (arrows).

FIGS. 10A and 10B are photographs similar to FIGS. 9A and 9B, except that the animal received c-myc antisense oligonucleotide (SEQ ID NO:1) in lieu of the sense oligonucleotide. A marked reduction of the neointima is noted.

DETAILED DESCRIPTION OF THE PRESENT INVENTION

Figure 1:
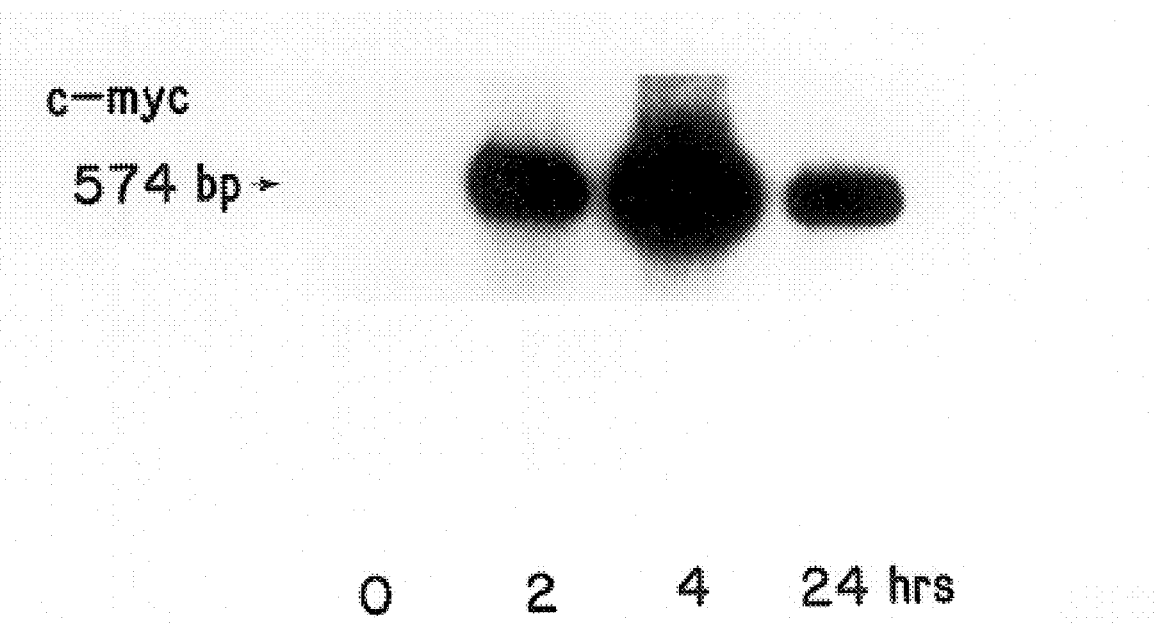
FIG. 1 is an autoradiogram of c-myc mRNA in quiescent and proliferating human SMCs electrophoresed in a denaturing 6% polyacrylamide gel.

Antisense oligonucleotides hold great promise as therapeutic agents for the treatment of many human diseases. Conceptually, it is much easier to design compounds which interact with a primary structure such as an RNA molecule by base pairing than it is to design a molecule to interact with the active site of an enzyme. oligonucleotides specifically bind (hybridize) to the complementary sequence of DNA, pre-mRNA or mature mRNA, as defined by Watson-Crick or Hoogsteen base pairing, interfering with the flow of genetic information from DNA to protein. The properties of antisense oligonucleotides which make them specific for their target sequence also make them extraordinarily versatile. Because antisense oligonucleotides are long chains of four monomeric units, they may be readily synthesized for any target sequence. Numerous recent studies have documented the utility of antisense oligonucleotides as biochemical tools for studying target proteins, Rothenberg et al., *J. Natl. Cancer Inst.* 1989, 81, 1539–1544; Zon, G., *Pharmaceutical Res.* 1988, 5, 539–549. Because of recent advances in oligonucleotide chemistry and synthesis of nuclease resistant oligonucleotides which exhibit enhanced stability, it is now possible to consider the use of antisense oligonucleotides as a novel form of therapeutics.

Current methods of treating or preventing the occurrence of restenosis exhibit only limited effectiveness in treating or preventing restenosis. The present invention, directed to modulation of the proliferation of smooth muscle cells, meets needs heretofore unmet.

The term "oligonucleotide" as used herein refers to a polynucleotide formed from joined nucleotides. Moreover, the term "oligonucleotide" includes naturally occurring oligonucleotides or synthetic oligonucleotides formed from naturally occurring subunits or analogous subunits designed to confer special properties on the oligonucleotide so that it is more stable in biological systems or binds more tightly to target sequences. It also includes modifications of the oligonucleotides such as chemically linking them to other compounds that will enhance delivery to cells or to the nucleus and other compartments of cells. Further, oligonucleotides of the invention may contain modified internucleotide linkages to provide stability against nucleases. For example, the invention may include phosphorothioate oligodeoxyribonucleotides. Thus, the term "oligonucleotide" includes unmodified oligomers of ribonucleotides and/or deoxyribonucleotides, as well as oligomers wherein one or more purine or pyrimidine moieties, sugar moieties or internucleotide linkages is chemically modified.

Without limiting the generality of the foregoing, the term "oligonucleotide" as used herein includes linear oligomers of natural or modified monomers or linkages, including deoxyribonucleosides, ribonucleosides, α-anomeric forms thereof, polyamide nucleic acids, and the like, capable of specifically binding to a target polynucleotide by way of a regular pattern of monomer-to-monomer interactions, such as Watson-Crick type of base pairing, Hoogsteen or reverse Hoogsteen types of base pairing, or the like. Usually, monomers are linked by phosphodiester bonds or analogs thereof to form oligonucleotides ranging in size from a few monomeric units, e.g., 3–4, to several hundreds of monomeric units. Analogs of phosphodiester linkages include: phosphorothioate, phosphorodithioate, phosphoroselenoate, phosphorodiselenoate, phosphoroanilothioate, phosphoranilidate, phosphoramidate, and the like, as more fully described below. As used herein, "nucleoside" includes the natural nucleosides, including 2'-deoxy and 2'-hydroxyl forms, e.g., as described in Kornberg and Baker, *DNA Replication,* 2nd Ed. (Freeman, San Francisco, 1992). "Analogs" in reference to nucleosides includes synthetic nucleosides having modified base moieties and/or modified sugar moieties, e.g., described generally by Scheit, *Nucleotide Analogs* (John Wiley, New York, 1980). Such analogs include synthetic nucleosides designed to enhance binding properties, e.g., duplex or triplex stability, specificity, or the like.

An "antisense oligonucleotide specific for c-myc", or "c-myc antisense oligonucleotide" is an oligonucleotide having a sequence (i) capable of forming a stable triplex with a portion of the c-myc proto-oncogene, or (ii) capable of forming a stable duplex with a portion of an mRNA transcript of the c-myc proto-oncogene.

"Stability" in reference to duplex or triplex formation roughly means how tightly an antisense oligonucleotide binds to its intended target sequence; more precisely, it means the free energy of formation of the duplex or triplex under physiological conditions. Melting temperature under a standard set of conditions, e.g., as described below, is a convenient measure of duplex and/or triplex stability. Preferably, antisense oligonucleotides of the invention are selected that have melting temperatures of at least 50° C. under the standard conditions set forth below; thus, under physiological conditions and the preferred concentrations, duplex or triplex formation will be substantially favored over the state in which the antisense oligonucleotide and its target are dissociated. It is understood that a stable duplex or triplex may in some embodiments include mismatches between base pairs and/or among base triplets in the case of triplexes. Preferably, antisense oligonucleotides of the invention form perfectly matched duplexes and/or triplexes with their target polynucleotides.

It is preferred that the oligonucleotides of the invention be modified to increase stability and prevent intracellular and extracellular degradation. It is more preferred that the oligonucleotides of the invention be modified to increase their affinity for target sequences, and their transport to the appropriate cells and cell compartments when they are delivered into a mammal in a pharmaceutically active form.

Target polynucleotides may be single-stranded or double-stranded DNA or RNA; however, single-stranded DNA or RNA targets are preferred. It is understood that the target to which the c-myc antisense oligonucleotides of the invention are directed include allelic forms of the c-myc proto-oncogene. There is substantial guidance in the literature for selecting particular sequences for antisense oligonucleotides given a knowledge of the sequence of the target polynucleotide, e.g., Peyman and Ulmann, *Chemical Reviews,* 90:543–584, 1990; Crooke, *Ann. Rev. Pharmacal. Toxicol.,* 32:329–376 (1992); and Zamecnik and Stephenson, *Proc. Natl. Acad. Sci.,* 75:280–284 (1974). Preferably, the sequences of c-myc antisense compounds are selected such that the G-C content is at least 60%. Preferred proto-oncogene mRNA targets include the 5'cap site, tRNA primer binding site, the initiation codon site, the mRNA donor splice site, and the mRNA acceptor splice site, e.g., Goodchild et al., U.S. Pat. No. 4,806,463.

Antisense oligonucleotides of the invention may comprise any polymeric compound capable of specifically binding to a target polynucleotide by way of a regular pattern of monomer-to-nucleoside interactions, such as Watson-Crick type of base pairing, Hoogsteen or reverse Hoogsteen types of base pairing, or the like. Antisense compounds of the invention may also contain pendent groups or moieties, either as part of or separate from the basic repeat unit of the polymer, to enhance specificity, nuclease resistance, delivery, or other property related to efficacy, e.g., cholesterol moieties, duplex intercalators such as acridine, poly-L-lysine, "end-capping" with one or more nuclease-resistant linkage groups such as phosphorothioate, and the like.

For example, it is known that enhanced lipid solubility and/or resistance to nuclease digestion results by substituting an alkyl group or alkoxy group for a phosphate oxygen in the internucleotide phosphodiester linkage to form an alkylphosphonate oligonucleoside or alkylphosphotriester oligonucleotide. Non-ionic oligonucleotides such as these are characterized by increased resistance to nuclease hydrolysis and/or increased cellular uptake, while retaining the ability to form stable complexes with complementary nucleic acid sequences. The alkylphosphonates, in particular, are stable to nuclease cleavage and soluble in lipid. The preparation of alkylphosphonate oligonucleosides is disclosed in Tso et al., U.S. Pat. No. 4,469,863.

Preferably, nuclease resistance is conferred on the antisense compounds of the invention by providing nuclease-resistant internucleosidic linkages. Many such linkages are known in the art, e.g., phosphorothioate: Zon and Geiser, *Anti-Cancer Drug Design,* 6:539–568 (1991); Stec et al., U.S. Pat. No. 5,151,510; Hirschbein, U.S. Pat. No. 5,166,387; Bergot, U.S. Pat. No. 5,183,885; phosphorodithioates: Marshall et al., *Science,* 259:1564–1570 (1993); Caruthers and Nielsen, International application PCT/US89/02293; phosphoramidates, e.g., —OP (=O) (NR$^1$R$^2$)—O— with R$^1$ and R$^2$ hydrogen or $C_1$–$C_3$ alkyl; Jager et al., *Biochemistry,* 27:7237–7246 (1988); Froehler et al., International application PCT/US90/03138; peptide nucleic acids: Nielsen et al., *Anti-Cancer Drug Design,* 8: 53–63 (1993), International application PCT/EP92/01220; methylphosphonates: Miller et al., U.S. Pat. No. 4,507,433, Ts'o et al., U.S. Pat. No. 4,469,863; Miller et al., U.S. Pat. No. 4,757,055; and P-chiral linkages of various types, especially phosphorothioates, Stec et al., European patent application 506,242 (1992) and Lesnikowski, *Bioorganic Chemistry,*

21:127–155 (1993). Additional nuclease linkages include phosphoroselenoate, phosphorodiselenoate, phosphoroanilothioate, phosphoranilidate, alkylphosphotriester such as methyl- and ethylphosphotriester, carbonate such as carboxymethyl ester, carbamate, morpholino carbamate, 3'-thioformacetal, silyl such as dialkyl ($C_1$–$C_6$)- or diphenylsilyl, sulfamate ester, and the like. Such linkages and methods for introducing them into oligonucleotides are described in many references, e.g., reviewed generally by Peyman and Ulmann, *Chemical Reviews* 90:543–584 (1990); Milligan et al., *J. Med. Chem.*, 36:1923–1937 (1993); Matteucci et al., International application PCT/US91/06855.

Resistance to nuclease digestion may also be achieved by modifying the internucleotide linkage at both the 5' and 3' termini with phosphoroamidites according to the procedure of Dagle et al., *Nucl. Acids Res.* 18, 4751–4757 (1990).

Preferably, phosphorous analogs of the phosphodiester linkage are employed in the compounds of the invention, such as phosphorothioate, phosphorodithioate, phosphoramidate, or methylphosphonate. More preferably, phosphorothioate is employed as the nuclease resistant linkage.

Phosphorothioate oligonucleotides contain a sulfur-for-oxygen substitution in the internucleotide phosphodiester bond. Phosphorothioate oligonucleotides combine the properties of effective hybridization for duplex formation with substantial nuclease resistance, while retaining the water solubility of a charged phosphate analogue. The charge is believed to confer the property of cellular uptake via a receptor (Loke et al., *Proc. Natl. Acad. Sci.*, 86, 3474–3478 (1989)).

It is understood that in addition to the preferred linkage groups, compounds of the invention may comprise additional modifications, e.g., boronated bases, Spielvogel et al., U.S. Pat. No. 5,130,302; cholesterol moieties, Shea et al., *Nucleic Acids Research*, 18:3777–3783 (1990) or Letsinger et al., *Proc. Natl. Acad. Sci.*, 86:6553–6556 (1989); and 5-propynyl modification of pyrimidines, Froehler et al., *Tetrahedron Lett.*, 33:5307–5310 (1992).

Oligonucleotides of the invention may be synthesized by any method known in the art. It is preferred in the present invention that the oligonucleotides be prepared using synthetic chemical methods, such as, for example, phosphoramidite chemistry by sulfurization with tetraethylthiuram disulfide in acetonitrile. See, for example, Vu and Hirschbein, *Tetrahedron Lett.* 1991, 32, 30005–30008. Oligonucleotides of the invention may also be synthesized using in vitro and in vivo transcription systems, such as transcription by $T^7$ polymerase or expression vectors. Oligonucleotides synthesized using in vitro and in vivo transcription systems may be modified via chemical methods known to those skilled in the art. Examples of such modifications include encapsulation in liposomes, or chemical linkage to steroids, antibodies, and cell receptor ligands.

In embodiments where triplex formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g., whether ribose or deoxyribose nucleosides are employed), base modifications (e.g., methylated cytosine, and the like) in order to maximize, or otherwise regulate, triplex stability as desired in particular embodiments, e.g., Roberts et al., *Proc. Natl. Acad. Sci.*, 88:9397–9401 (1991); Roberts et al., *Science*, 258:1463–1466 (1992); Distefano et al., *Proc. Natl. Acad. Sci.*, 90:1179–1183 (1993); Mergny et al., *Biochemistry*, 30:9791–9798 (1992); Cheng et al., *J. Am. Chem. Soc.*, 114:4465–4474 (1992); Beal and Dervan, *Nucleic Acids Research*, 20:2773–2776 (1992); Beal and Dervan, *J. Am. Chem. Soc.*, 114:4976–4982; Giovannangeli et al., *Proc. Natl. Acad. Sci.*, 89:8631–8635 (1992); Moser and Dervan, *Science*, 238:645–650 (1987); McShan et al., *J. Biol. Chem.*, 267: 5712–5721 (1992); Yoon et al., *Proc. Natl. Acad. Sci.*, 89:3840–3844 (1992); and Blume et al., *Nucleic Acids Research*, 20:1777–1784 (1992).

The length of the oligonucleotide moieties is sufficiently large to ensure that specific binding will take place only at the desired target polynucleotide and not at other fortuitous sites, as explained in many references, e.g., Rosenberg et al., International application PCT/US92/05305; or Szostak et al., *Meth. Enzymol*, 68:419–429 (1979). The upper range of the length is determined by several factors, including the inconvenience and expense of synthesizing and purifying large oligomers, the greater tolerance of longer oligonucleotides for mismatches than shorter oligonucleotides, whether modifications to enhance binding or specificity are present, whether duplex or triplex binding is desired, and the like.

It is preferred that the length of the oligonucleotide be between 5 and 200 nucleotides. It is more preferred that the oligonucleotide be between 10 and 50 nucleotides in length. It is most preferred that the oligonucleotide be between 15 and 25 nucleotides in length. In preferred embodiments, the oligonucleotide is specifically hybridizable with a translation initiation site. In one preferred embodiment of the present invention the oligonucleotide has the sequence 5' AACGTTGAGGGGCAT 3' (SEQ ID NO: 1). This oligonucleotide is complementary to a segment of the c-myc mRNA beginning with a translation initiation codon and extending downstream therefrom. The translation initiation codon comprises nucleotides 559–562 of the c-myc mRNA. The coding region comprising nucleotides 559–1875 is flanked by a 5' noncoding region, and a 3' noncoding region extending to nucleotide 2121.

In general, the antisense oligonucleotides used in the practice of the present invention will have a sequence which is completely complementary to a selected portion of the target polynucleotide. Absolute complementarity is not however required, particularly in larger oligomers. Thus, reference herein to a "nucleotide sequence complementary to" a target polynucleotide does not necessarily mean a sequence having 100% complementarity with the target segment. In general, any oligonucleotide having sufficient complementarity to form a stable duplex with the target (e.g. the c-myc mRNA) that is, an oligonucleotide which is "hybridizable", is suitable. Stable duplex formation depends on the sequence and length of the hybridizing oligonucleotide and the degree of complementarity with the target polynucleotide. Generally, the larger the hybridizing oligomer, the more mismatches may be tolerated. One skilled in the art may readily determine the degree of mismatching which may be tolerated between any given antisense oligomer and the target sequence, based upon the melting point, and therefore the thermal stability, of the resulting duplex.

Preferably, the thermal stability of hybrids formed by the antisense oligonucleotides of the invention are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and antisense oligonucleotide concentrations at between about 1.0–2.0 µM. Typical conditions are as follows: 150 mM NaCl and 10 mM $MgCl_2$ in a 10 mM sodium phosphate buffer (pH 7.0) or in a 10 mM Tris-HCl buffer (pH 7.0). Data for melting curves are accumulated by heating a sample of the antisense oligonucleotide/target polynucleotide complex from room temperature to about 85–90° C. As the temperature of the sample increases, absorbance of 260 nm light is monitored at 1° C. intervals, e.g., using a Cary (Australia) model 1E or a Hewlett-Packard (Palo Alto, Calif.) model HP 8459 UV/VIS spectrophotometer and model HP 89100A temperature controller, or like instruments. Such techniques provide a convenient means for measuring and comparing the binding strengths of antisense oligonucleotides of different lengths and compositions.

According to one embodiment, the oligonucleotides of this invention are designed to be hybridizable with messenger RNA derived from the c-myc gene. Such hybridization, when accomplished, interferes with the normal roles of the messenger RNA to cause a modulation of its function in the cell. The functions of messenger RNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with the RNA function is to modulate expression of the c-myc gene. By modulating the expression of the c-myc gene, smooth muscle cell proliferation is modulated, or inhibited.

In preferred embodiments of the present invention smooth muscle cell proliferation associated with restenosis may be targeted. Thus, smooth muscle cells are preferably vascular smooth muscle cells such as smooth muscle cells of the arteries, veins and capillaries.

For therapeutic or prophylactic treatment, oligonucleotides are administered in accordance with this invention. Oligonucleotides may be formulated in a pharmaceutical composition, which may include carriers, thickeners, diluents, buffers, preservatives, surface active agents and the like in addition to the oligonucleotide. In some embodiments of the present invention, the oligonucleotide may be administered in conjunction with other therapeutics found effective to limit or eliminate restenosis, such as, for example, anti-platelet, anti-coagulation, anti-inflammatory, and vasodilation therapeutics. The solution may also contain a proteolytic enzyme such as disparse, trypsin, collagenase, papain, pepsin, or chymotrypsin. In addition to proteolytic enzymes, lipases may be used. As a mild detergent, the solution may contain NP-40, Triton X100, deoxycholate, SDS or the like.

Antisense compounds of the invention include the pharmaceutically acceptable salts thereof, including those of alkaline earths, e.g., sodium or magnesium, ammonium or $NX_4^+$, wherein X is $C_1$–$C_4$ alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as $Na^+$, $NH_4^+$, or the like.

The pharmaceutical composition may be administered in a number of ways depending on whether local or systemic treatment is desired, and on the area to be treated. Administration may be accomplished by methods known to those skilled in the art such as intravenously or by use of a catheter to direct treatment to an affected area. Intravascular devices and their use are known to those skilled in the art.

Local administration to the relevant traumatized vessel by way of a catheter is one form of delivery. The c-myc antisense oligonucleotide is administered in the vicinity of the lesion via a catheter from inside the lumen, e.g., a porous balloon as described by Wolinsky and Thung, *JACC* 15: 475–481 (1990), or through the adventitia (i.e., the most outer layer of the vessel wall) with materials aiding slow release of antisense compound, e.g., a pluronic gel system as described by Simons et al., *Nature* 359: 67–70 (1992). Other slow release techniques for local delivery include coating stents with antisense compound, e.g., using a binder or gel described in Wilensky et al., *Trends in Cardiovascular Med.* 3:163–170 (1993). A dose delivered at the target lesion is in the range of from 1 µg to 100 mg; and more preferably, the dose range is between 1 µg and 5 mg. Preferably, the delivery time is in the range of about 30 seconds to 60 minutes, and more preferably, in the range of about 30 seconds to about 1–2 minutes, e.g., Zalewski et al., pages 79–87 in Goldberg, editor, *Coronary Angioplasty* (Davis, Philadelphia, 1988).

Systemic, intravenous, administration is also contemplated. Without wishing to be bound by any theory, it is believed that certain organs of the body may provide a repository for oligonucleotide that will return to the circulation over a longer period of time than previously expected. It is believed that such depot organs, particularly the kidney and liver, can be the source of oligonucleotide accumulating in vessels for up to 72 hours post administration.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The following examples are illustrative but are not meant to be limiting of the present invention.

EXAMPLE 1

Cell culture

Human SMCs originated from the saphenous veins of patients undergoing routine bypass surgery. The cells were isolated by an explant method. The explants were placed into tissue culture dishes containing Dulbecco's modified: Eagle's medium (DMEM) supplemented with 20% heat inactivated fetal bovine serum (FBS), 100 IU/ml penicillin, 100 µg/ml streptomycin, and 2 mM/ml glutamine (20% FBS-DMEM). The cultures were maintained at 37° C. in a humidified incubator with 5% $CO_2$. The cells exhibited typical morphological characteristics of vascular SMCs, i.e., spindle shape and hill-and-valley pattern. The identification of vascular SMCs was further confirmed by in situ smooth muscle alpha-actin staining.

EXAMPLE 2

Synthesis of Oligonucleotides 15-mer antisense, sense and mismatched oligonucleotides were synthesized on an Applied Biosystems model 394 high throughput DNA synthesizer (Applied Biosystems, Foster City, Calif.). Larger quantities for in vivo studies were synthesized on an Applied Biosystems modified 390Z large scale DNA synthesizer. The oligonucleotides were lyophilized, resuspended in PBS and quantified by spectrophotometry. Modified (phosphorothioate) oligonucleotides from the translation initiation region of human c-myc gene were employed in this study. The sequences were as follows: sense oligonucleotide (5' ATGCCCCTCAACGTT 3'; SEQ ID NO: 2), antisense oligonucleotide (5' AACGTTGAGGGGCAT 3'; SEQ ID NO: 1), and mismatched oligonucleotide (5' TACGGGGTTGAGCAA 3'; SEQ ID NO: 3).

EXAMPLE 3

Growth Assay

The early passages (2 and 4) of human SMCs in 20% FBS-DMEM were seeded at a density of 10,000 cells per well in 24-well plates. Twenty four hours after plating, original medium was replaced with growth arrest medium (0.5% FBS-DMEM) for the next 48 hours. Then the cell growth was synchronized by the addition of 20% FBS-DMEM. The oligonucleotides were added 24 hours prior to stimulation, at the time of stimulation and every 48 hours thereafter unless stated otherwise in the text. At the times indicated, SMCs were trypsinized and counted in a Coulter counter. The degree of inhibition was calculated as follows:

% inhibition=1−(net growth of antisense-treated cells/net growth of sense-treated cells)×100.

The net growth of human SMCs was obtained by subtracting the starting cell number (at the time the cells are released from $G_o$ phase) from the cell number at indicated time points of the experiment. Each experiment was carried out in triplicate. Data are expressed as mean±SD.

EXAMPLE 4

Cellular UPtake of Oligonucleotides

SMCs were grown in 100 mm plates supplemented with 20% FBS-DMEM. After growth arrest for 48 hours (0.5% FBS-DMEM), SMCs were synchronized with 20% FBS-DMEM. To determine cellular uptake of oligonucleotides, SMCs were incubated with 2 $\mu$M of $^{32}$P-end labeled oligonucleotides ($5 \times 10^6$ cpm/$\mu$g) for 1, 3, 6, 16, 24 and 36 hours. Following incubation, cells were washed in PBS and 0.2 M glycine (pH 2.8) to remove membrane-bound oligonucleotides. The remaining cell-associated radioactivity which represents intracellular uptake of oligonucleotides was measured in a scintillation counter. The uptake of oligonucleotides by human SMCs was expressed as pmol/$10^5$ cells.

EXAMPLE 5

Reverse Transcription and Polymerase Chain Reaction (RT-PCR)

To determine c-myc mRNA levels in human SMCs, a modified RT-PCR technique was used. Total RNA was isolated with a single step procedure using acid guanidinium thiocyanatephenol-chloroform extraction method. In order to distinguish between amplification of genomic DNA and cDNA, the primer pairs were designed to enclose at least one intron on the genomic sequence of c-myc. The primers were synthesized as described above and the primer sequences were as follows: primer A, 5' TGGTGCTCCATGAGGAGACA 3' (SEQ ID NO: 4); primer B, 5' GTGTTTCAACTGTTCTCGTC 3' (SEQ ID NO: 5). The primers were 5' end-labeled with 50 $\mu$Ci of ($\gamma$-32P)-ATP according to 5' DNA terminus labeling protocol (GIECO BRL Life Technologies, Inc. Gaithersburg, Md.). Two $\mu$g of total RNA was reverse transcribed into cDNA by 200 units of SuperScript reverse transcriptase. The PCR amplification of cDNA was carried out using the GeneAmp RNA PCR protocol (Perkin-Elmer Corp, Hayward, Calif.). Briefly, aliquot of cDNA was added to a reaction mixture containing 20 $\mu$M of primers and 5 units of Taq polymerase. Amplification was performed using a DNA thermal cycler (Perkin-Elmer Cetus) for 30 cycles. A cycle profile consisted of 1 minute at 94° C. for denaturation, 2 minutes at 60° C. for annealing, and 2 minutes at 72° C. for primer extension. The RT-PCR products were electrophoresed in a 6% polyacrylamide gel and exposed to Kodak film.

EXAMPLE 6

C-myc Proto-oncogene Expression in Human SMCs

To assess the level of expression of the c-myc proto-oncogene in human SMCs, c-myc mRNA was determined in quiescent (arrested for 48 hours) and proliferating (2, 4, and 24 hours after serum stimulation) cells. RT-PCR was performed as described in Example 5 using specific c-myc primers. FIG. 1 is an autoradiogram of amplified mRNA from quiescent and proliferating cells. As can be seen in FIG. 1, quiescent human SMCs expressed a low level of c-myc mRNA. In contrast in proliferating SMCs, c-myc mRNA levels increased at 2 and 4 hours following cell growth stimulation. The c-myc mRNA declined at 24 hours, although its level remained higher than in quiescent cells.

EXAMPLE 7

Inhibition of SMC Proliferation

Figure 2:
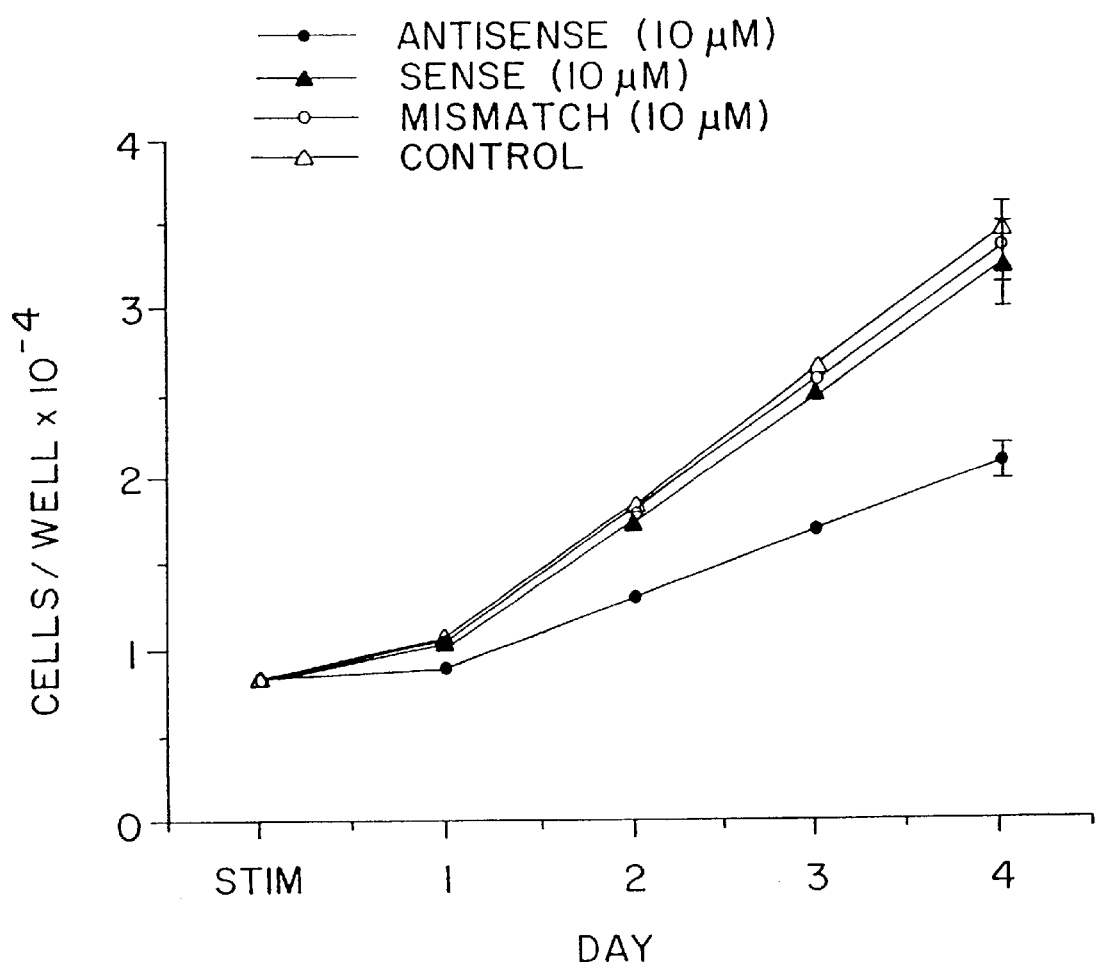
FIG. 2 is a schematic representation of growth curves of human SMCs incubated with 10 $\mu$M of c-myc antisense (filled circle), sense (filled triangle), and mismatched (open circle) oligonucleotides. Control cells (open triangle) were incubated without addition of oligonucleotides.

Human SMCs were incubated with c-myc antisense phosphorothioate oligonucleotides as described in Example 3. The experiments were carried out in triplicate and repeated three times on different occasions yielding similar results. Results are presented as mean±SD. As can be seen in FIG. 2, the incubation of human SMCs with c-myc antisense phosphorothioate oligonucleotides resulted in a significant growth-inhibitory effect, whereas sense or mismatched oligonucleotides exerted no effect on cell growth. A significant inhibition was maintained for at least 4 days with a continuous exposure to oligonucleotides (p<0.01). In contrast to the growth-inhibitory effect of phosphorothioate oligonucleotides, unmodified antisense oligonucleotides had no effect on SMC growth in doses up to 40 $\mu$M.

Figure 3:
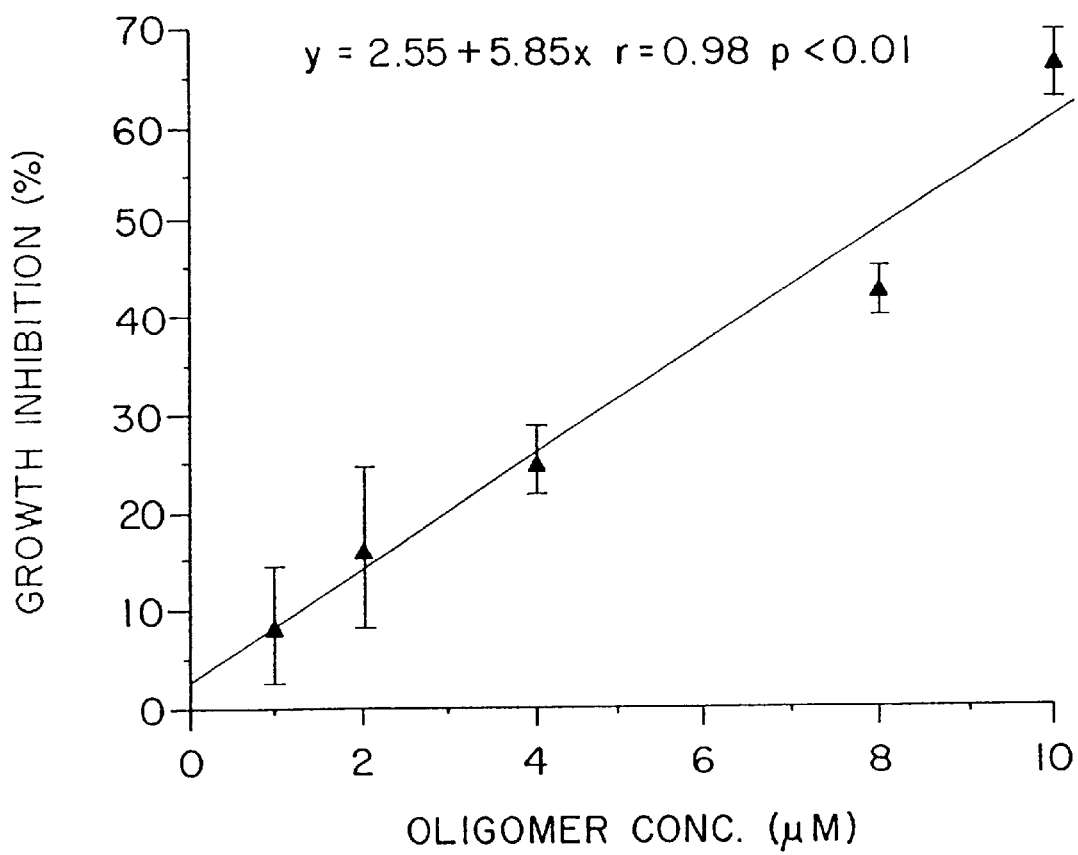
FIG. 3 is a schematic representation of dose-dependent growth inhibition of human SMCs following the addition of c-myc antisense oligonucleotides. Results are expressed as mean±SD. Conc. denotes concentration.

Growth assays performed in accordance with Example 3 also showed that, as expected, the antiproliferative effect of c-myc antisense phosphorothioate oligonucleotides was dose-dependent within a range of 1 to 10 $\mu$M, as shown in FIG. 3. In addition, without pretreatment, the incubation of human SMCs with c-myc antisense oligonucleotides (10 $\mu$M) for 8 and 24 hours produced comparable growth inhibition of 58±13% and 70±14%, respectively.

Similar studies were carried out to determine the growth inhibitory effect of c-myc antisense oligonucleotides in porcine SMCs. Growth inhibition exceeding 90% was observed following c-myc antisense treatment (12 μM) as compared with control or sense-treated porcine SMCs. In all growth experiments, the treated SMCs demonstrated normal morphology and no cell death was noted at the tested dose range.

To assess potential long-term effect of c-myc antisense treatment on cell growth, the oligonucleotides were withdrawn after 8 hours of incubation and human SMCs were subcultured 7 days later. The cell counts were obtained at 1, 2, 4 and 6 days thereafter. The growth rates of antisense-treated and control SMCs were identical. This demonstrates normal SMC viability after antisense oligonucleotide treatment.

Figure 4:
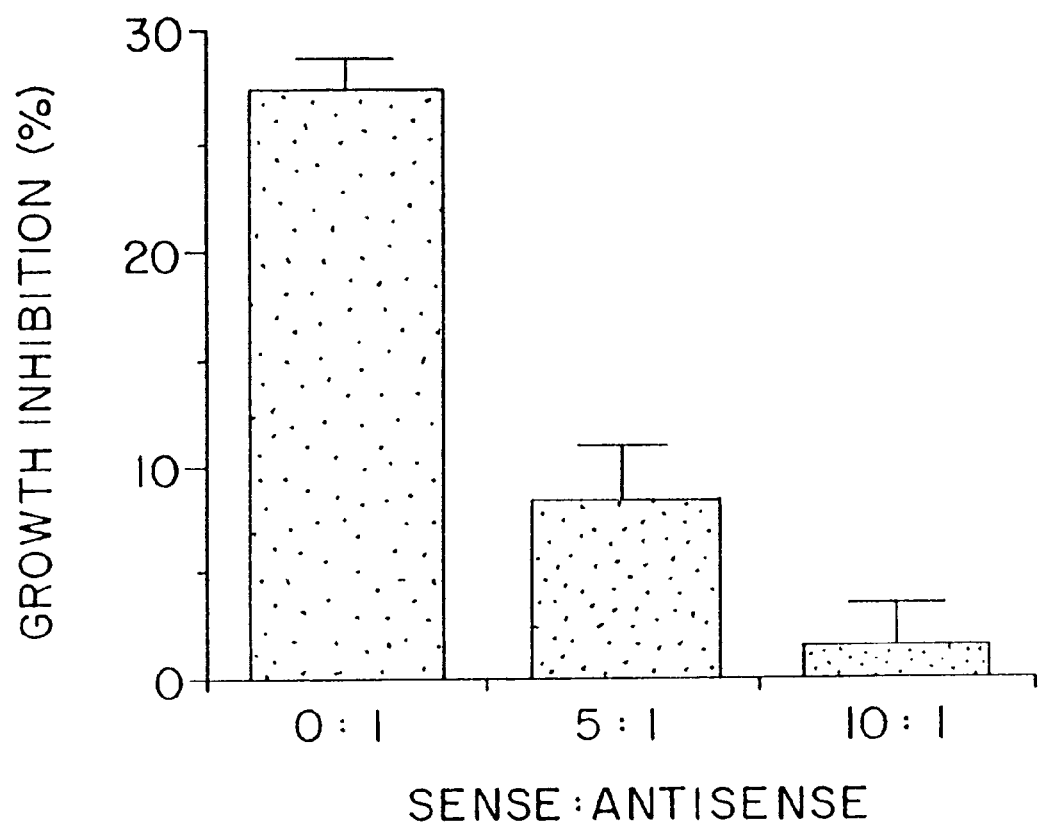
FIG. 4 is a schematic representation of the effect of excess sense oligonucleotide on the growth-inhibitory effect of c-myc antisense oligonucleotides. Percent inhibition at day 1 was calculated in triplicate. Data represent mean±SD.

We expected that antiproliferative effect of c-myc antisense oligonucleotides would be abrogated by the addition of excess sense oligonucleotides to the SMC culture. As shown in FIG. 4, increasing the ratio of sense to antisense oligonucleotides completely abolished the growth inhibition. This was likely due to formation of heteroduplexes between the two oligonucleotides which indicates sequence-specific growth inhibition of antisense oligonucleotides.

EXAMPLE 8

Inhibition of c-myc Expression

Figure 5:
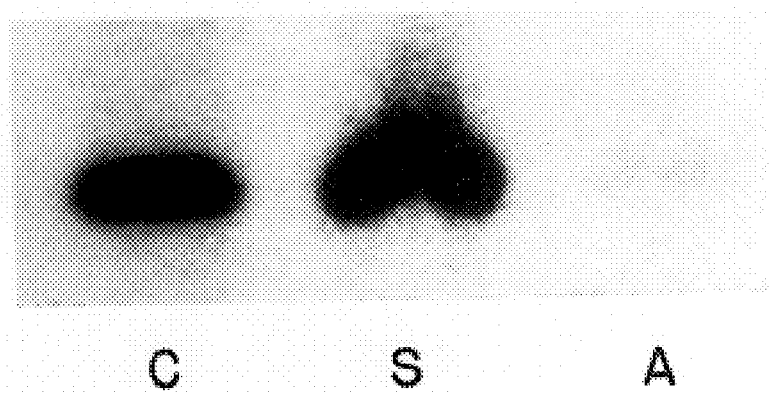
FIG. 5 is an autoradiogram of a gel of c-myc mRNA from human SMCs treated with sense or antisense oligonucleotide, electrophoresed in a denaturing 6% polyacrylamide gel. C: control (no oligonucleotide), S: c-myc sense oligonucleotides (10 $\mu$M), A: c-myc antisense oligonucleotide (10 $\mu$M).

In order to determine if the antiproliferative effect of antisense oligonucleotides was due to a reduction in c-myc expression, c-myc mRNA was determined in antisense and sense-treated cells as described in Example 5. FIG. 5 shows that c-myc antisense phosphorothioate oligonucleotides (10 μM) reduced the target mRNA in proliferating human SMCs, whereas sense-treated cells demonstrated unchanged level of c-myc mRNA as compared with that in cells without oligonucleotide treatment.

EXAMPLE 9

Cellular Uptake and Intracellular Kinetics of Oligonucleotides

Figure 6:
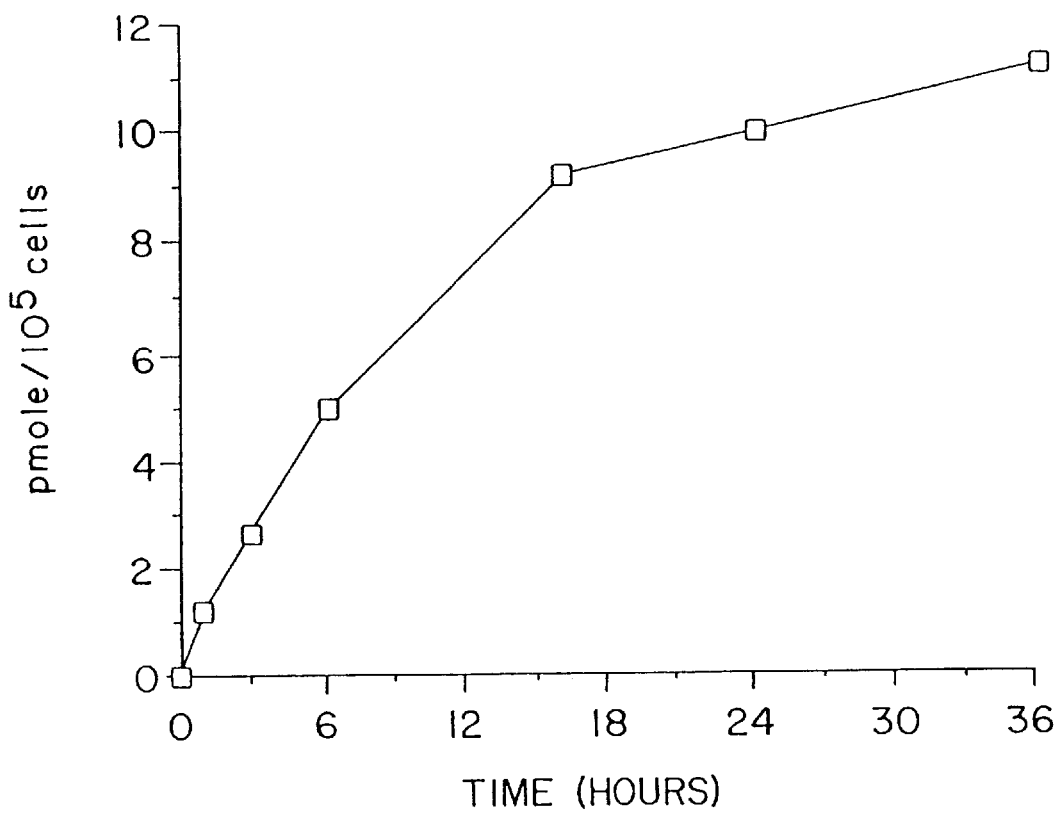
FIG. 6 is a schematic representation of intra-cellular accumulation of oligonucleotides in human SMCs. Intracellular content of oligonucleotides was derived from cell associated radioactivity measured in a scintillation counter.

The kinetics of cellular uptake of oligonucleotides in human SMCs are shown in FIG. 6. Cells were incubated with 2 μM $^{32}$P-end labeled phosphorothioate oligonucleotides beginning at the time of cell stimulation. At indicated time points, cells were washed in PBS and 0.2M glycine (pH 2.8). SMC associated radioactivity was detectable as early as 1 hour after incubation and rapidly continued to increase until 16 hours. There was no difference in cellular uptake of $^{32}$P-end labeled oligonucleotides between quiescent and proliferating cells. Similar results were obtained using fluorescent activated cell sorter with FITC-labeled oligonucleotides.

Since cell associated radioactivity may not only represent intact oligonucleotides, but also degraded oligonucleotides containing $^{32}$P labeling or $^{32}$P incorporated in cellular macromolecules, the accumulation of intact oligonucleotides in human SMCs was determined. The intracellular concentration of intact oligo-nucleotides increased over 24 hour period and a similar amount of undegraded oligonucleotides remained within SMCs for at least the next 12 hours (i.e., 36 hours after exposure). Therefore, despite a short intracellular half-life, phosphorothioate oligonucleotide stability in serum and a rapid cellular uptake allowed for their sustained levels within human SMCs.

EXAMPLE 10

Pharmacokinetics of Oligomers in Coronary Arteries

Figure 7:
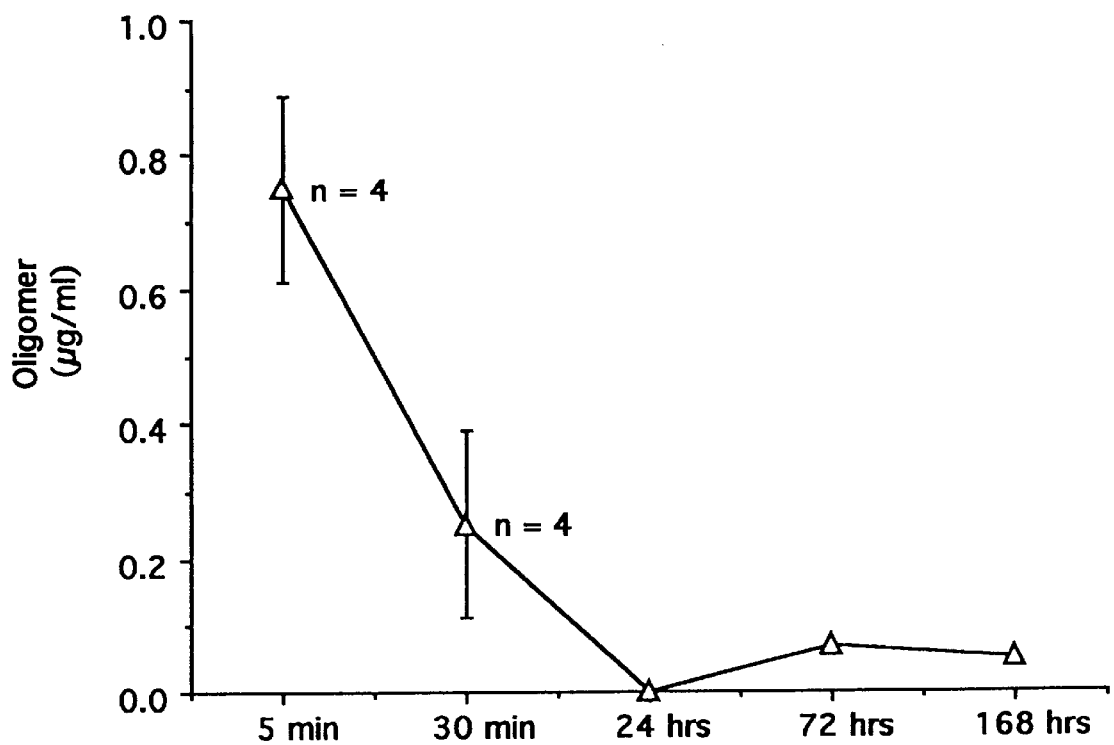
FIG. 7 is a schematic representation of the pharmacokinetics of $^{35}$S-labeled oligomer in plasma of pigs following injection of oligomer into coronary arteries (1 mg/vessel) via a porous balloon catheter under 4 atm. pressure. The animals were sacrificed at 30 min., 1, 3 and 7 days after delivery of oligonucleotides.

To determine the efficiency of intramural delivery and pharmacokinetics of oligomers in vivo, c-myc antisense oligonucleotides were labelled with $^{35}$S. Following localized balloon injury as described in Example 11, equal amounts of labeled oligonucleotides were injected into porcine coronary arteries (1 mg/vessel) at the site of the injury, through a porous balloon catheter under 4 atmospheres pressure. The delivery time was 26±4 seconds. The animals were sacrificed at 30 min., 1, 3 and 7 days after oligonucleotide delivery. The treated coronary arteries were excised and homogenized (weight 75–100 mg/vessel). The radioactivity in the sample was counted in a scintillation counter. The amounts of oligonucleotides were quantified according to a standard prepared with a known quantity of $^{35}$S-labeled oligonucleotides. The results are shown in FIGS. 7 (plasma oligomer) and 8 (coronary artery oligomer). The organ distribution of oligonucleotides as a function of time post delivery is provided in the table:

TABLE 1

| | Oligonucleotide organ concentration (μg per gram of tissue) | | | |
|---|---|---|---|---|
| Organ | 30 min | 1 day | 3 days | 7 days |
| Bone marrow | 0.37 | 0.38 | 0.46 | 0.45 |
| Small intestine | 0.53 | 0.51 | 0.48 | 0.11 |
| Cardiac muscle | 0.45 | 0.38 | 1.14 | 0.34 |
| Skelatal muscle | 0.34 | 0.25 | 0.29 | 0.35 |
| Lung | 0.49 | 0.42 | 0.43 | 0.35 |
| Liver | 2.18 | 2.39 | 1.71 | 0.73 |
| Kidney | 10.12 | 4.8 | 0.70 | 0.57 |
| Remote arteries (not injured) | 0.0 | 0.0 | 0.0 | 0.0 |

FIG. 7 indicates the plasma levels of oligonucleotides. There was a rapid clearance of oligomers from plasma, with a plasma clearance half-life of about 20 minutes. Although the concentration of oligonucleotides in plasma decreased to background levels at 24 hours after local delivery, an increase in oligonucleotide concentration in plasma was observed at 72 hours. The increased oligonucleotide level was sustained for an additional 96 hours. It is postulated that oligonucleotides were rapidly cleared from plasma and accumulated in the liver, kidney and cardiac muscle. These organs provided a repository for oligonucleotides that returned to the circulation over a longer period of time.

Figure 8:
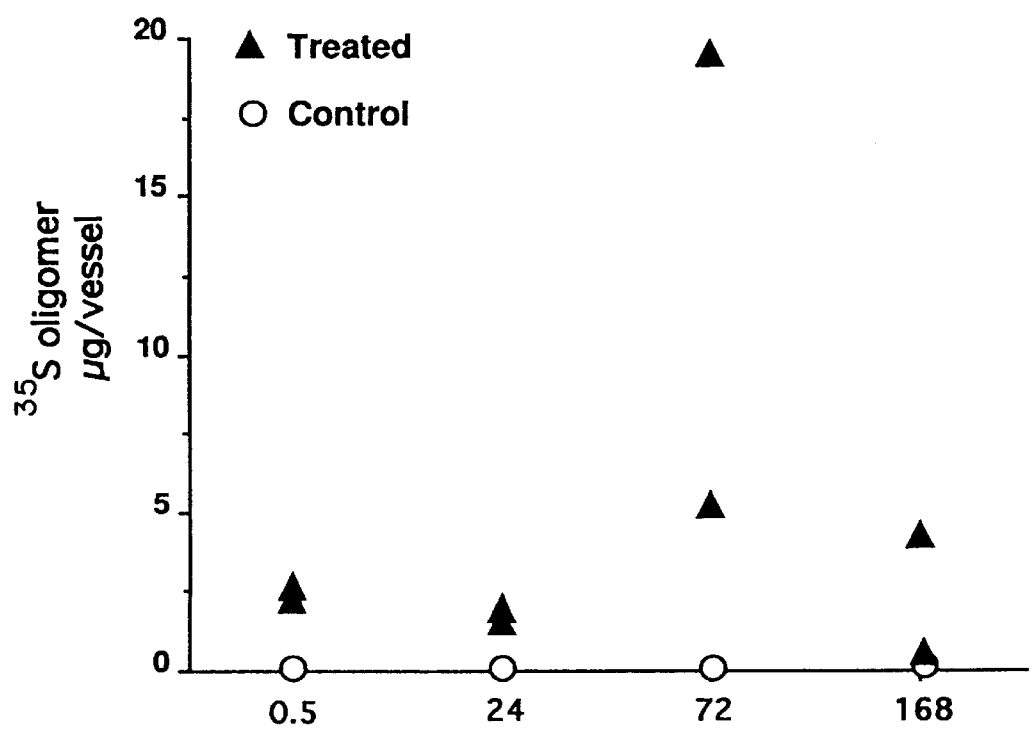
FIG. 8 is a schematic representation of the pharmacokinetics of $^{35}$S-labeled oligomer in the coronary arteries of the same pigs as in FIG. 7.

FIG. 8 is a schematic representation of the pharmacokinetics of oligonucleotides in coronary artery sites of localized baloon damage. Control vessels (no oligomer) showed no radioactivity at all time points, as indicated in Table 1. About 0.2% of oligomer was deposited into coronary artery sites of localized balloon damage. Of note, transcatheter delivery of oligomers afforded a higher concentration of oligonucleotides at the site of delivery (2–64 fold increase) as compared with various organs and remote arteries at 30 min. after injection. The concentration of oligonucleotides is increased in the arterial wall at 72 hours post injection. Of note, non-injured coronary arteries remote from the area of balloon damage demonstrated no accumulation of labeled oligomers at any time point. The possible explanation is that the vessel wall injury induces an inflammatory response and cell proliferation which may enhance cellular uptake of oligonucleotides. The oligonucleotides which returned to the cirulation from "storage" organs could be the source for redistribution to the injury site of the arterial wall.

Surprisingly, as a result of deposition of excess oligonucleotide (i.e., oligonucleotide dose not injected directly into the arterial wall) via plasma clearance to storage organs, a therapeutically sufficient arterial concentration of oligonucleotide may have been maintained by continuous leakage of the oligonucleotide from the storage organs into circulating plasma, augmented by enhanced uptake from plasma at the site of the injury.

The pharmacokinetic data in the porcine model suggest that a sustained level of oligonucleotides in the vessel wall is achievable with local catheter delivery. The data also indicate the potential for systemic treatment of restenosis using c-myc antisense oligonucleotides, since surprisingly very low concentrations in the circulating plasma may provide a therapeutically effective concentration at the site of injury.

The potential for therapeutic efficacy is surprisingly suggested by the in vivo animal study which follows. The in vitro studies described above (Example 7) achieved only partial inhibition of SMC growth at 10 μM oligonucleotide concentration, with continuous contact with human SMCs over four days. Notwithstanding, transient localized oligonucleotide application in vivo at a concentration of 20 μg/g vessel (≈6 μM), followed by uptake from depot organs, resulted in substantial reduction of neointima formation in a standard porcine restenosis model.

EXAMPLE 11

Animal Study—Inhibition of Restenosis by c-myc Antisense Oligonucleotide

The effectiveness of c-myc antisense compounds to inhibit restenosis was tested by administering c-myc-specific antisense (SEQ ID NO:1) and placebo (SEQ ID NO:2) oligonucleotide phosphorothioates to the site of coronary angioplasty in a standard porcine restenosis model using conventional protocols, e.g., see Karas et al., *J. Am. Coll. Card.* 20:467–474 (1992); and Schwartz et al., *Circulation* 82:2190–2200 (1990). Domestic crossbred pigs (*Sus scrofa*) were premedicated with oral aspirin (650 mg) prior to the study. General anesthesia consisted of intramuscular injection of ketamine (12 mg/kg) and xylazine (8 mg/kg). Additional doses of anesthesia were given intravenously throughout the experiment. After the right external carotid artery was surgically exposed, heparin (10,000 U) was administered to the pig intravenously. Using an 8 French SAL 1 guiding catheter (Medtronic Interventional Vascular, Inc., Danvers, Mass.) the coronary ostia were cannulated under fluoroscopic guidance. Prior to the delivery of the c-myc antisense and placebo, an oversized angioplasty balloon was used to injure the intimal and medial layers of the arterial walls by inflating at 10 atm and holding for 30 seconds three times in succession. Immediately after the angioplasty balloon was removed, intramural injections (2 ml) to the coronary arteries were carried out using a separate porous balloon. The c-myc antisense (13 replicates) or placebo (12 replicates) oligomers were injected under 4 atm of pressure and delivery was completed in an average of 27 seconds. The dose of oligomers was 1 mg per injured coronary artery. No adverse effects were associated with the delivery of the oligomers. One month after delivery, the animals were sacrificed and the maximal neointimal area (NA max), the neointimal thickness (NT max), and the residual lumen (RL) at the injury sites were determined by morphometry. The results (mean±SEM are shown in the table below and in attached FIGS. 9–11.

TABLE 2

| Oligomer | Replicates | NA max (mm²) | NT max (mm) | RL (%) |
|---|---|---|---|---|
| placebo | 12 | 0.80 ± 0.17 | 0.48 ± 0.09 | 64 ± 6 |
| antisense | 13 | 0.24 ± 0.06 | 0.20 ± 0.04 | 81 ± 5 |
| p | | <0.01 | <0.01 | <0.05 |

FIGS. 9A (mild injury) and 9B (severe injury) are photographs of a cross-section of an exemplary control (i.e., which received sense oligomer injection) coronary artery one month following injury. Histological injury score was graded as follows: Grade I: punctuated breaks in internal elastic lamina; neointima is present only on luminal side of internal elastic lamina; Grade II: gaps in internal elastic lamina with neointima visible on both sides of internal elastic lamina; Grade III: broken internal elastic lamina with neointima replacing ⅔ of media; Grade IV: broken internal elastic lamina with neointima extending to adventitia. The mild injury is based on injury score grade I and II, the severe injury is represented by grade III and IV. A significant neointimal thickness is noted in FIGS. 9A and 9B (arrows).

Figure 11:
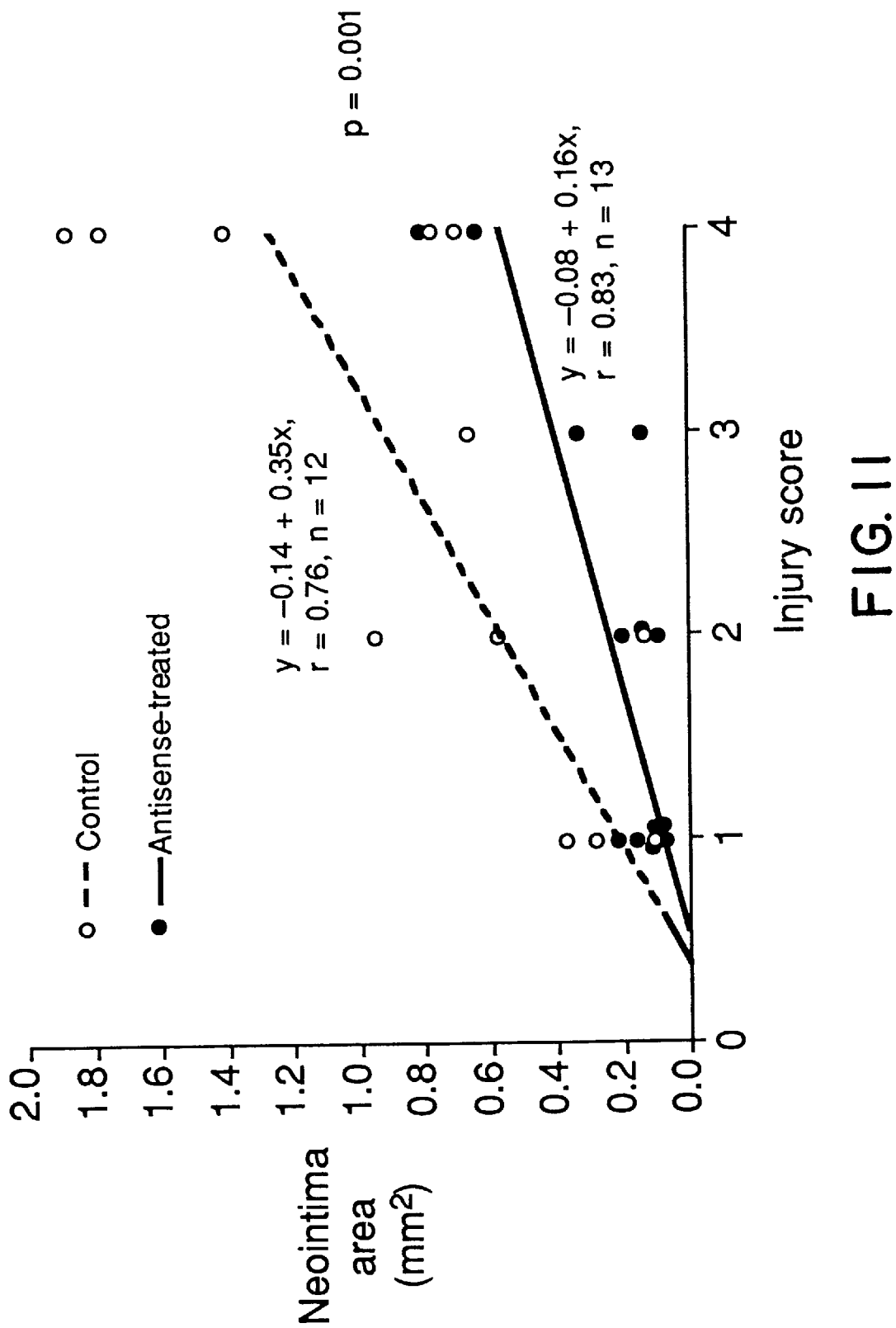
FIG. 11 is a schematic representation of the neointima area plotted as a function of the degree of coronary artery injury (injury score) induced in sense-treated (hollow circles) and antisense-treated (filled circles) pigs. Regression lines were drawn representing the relationship between neointima and injury score. The significant reduction in slope (p<0.01) reflects reduced neointimal formation in antisense-treated animals.

FIGS. 10A (mild injury) and 10B (severe injury) are photographs of a cross-section of an exemplary antisense-treated coronary artery. A marked reduction of the neointima is noted. When maximal neointimal area was analyzed as a function of degree of injury (FIG. 11), regression lines representing the relationship between neointima and injury-score (i.e., the severity of injury) showed a significant difference by slopes (p<0.01). As shown in FIG. 11, antisense oligomers significantly reduced neointimal formation, especially with more advanced injury.

In summary, these results show that local transcatheter delivery of c-myc antisense oligomers significantly reduces the formation of neointima in the coronary vasculature following balloon-induced injury of the arterial wall.

EXAMPLE 12

Growth Assay—Additional c-myc Antisense Oligonucleotides

The growth inhibitory effect of antisense oligonucleotides targeting regions of the c-myc mRNA apart from the translation initiation region were investigated as follows. Human SMC were plated at 5,000/cm² and arrested in 0.5% FBS for 48 hours. Cells were then stimulated with 20% FBS, and one of the following phosphorothioate oligomers (8 μM or 16 μM) complementary to various target sequences of the c-myc mRNA was added at the time of stimulation:

5' AAAGTGCCCG CCCGCTGCTG 3' (SEQ ID NO:6), targeting nucleotides 358–377 of the 5' non-coding region;

5' GGGAGAGTCG CGTCCTTGCT 3' (SEQ ID NO:7), targeting nucleotides 400–419 of the 5' non-coding region;

5' CCAGTGCAAA GTGCCCGCCC 3' (SEQ ID NO:8), targeting nucleotides 365–384 of the 5' non-coding region;

5' GGCCTTTTCA TTGTTTTCCA 3' (SEQ ID NO:9), targeting nucleotides 1709–1728 of the coding region;

5' TCATGGAGCA CCAGGGGCTC 3' (SEQ ID NO:10), targeting nucleotides 1264–1283 of the coding region;

5' CGGATCTCCC TTCCCAGGAC 3' (SEQ ID NO:11), targeting nucleotides 242–262 of the 5' non-coding region; and 5' CGTTCTTTTT TCCCGCCAAG 3' (SEQ IS NO:12), targeting nucleotides 80–89 of the 5' non-coding region.

5' AACGTTGAGG GGCAT 3' (SEQ ID NO:1), targeting the translation initiation region, served as a positive control. The following oligomers served as negative controls: translation initiation region sense oligomer (SEQ ID NO:2); mismatched oligomer 5' AACGTGGATT GGCAG (SEQ ID NO:13), which differs from SEQ ID NO:1 by four mismatches; and scrambled sense oligomer 5' GAACGGAGAC GGTTT 3' (SEQ ID NO:14). Cells were incubated with or without oligomers for 3 days and cell number was counted in a Coulter counter. Growth and inhibition was calculated as described previously.

Figure 12:
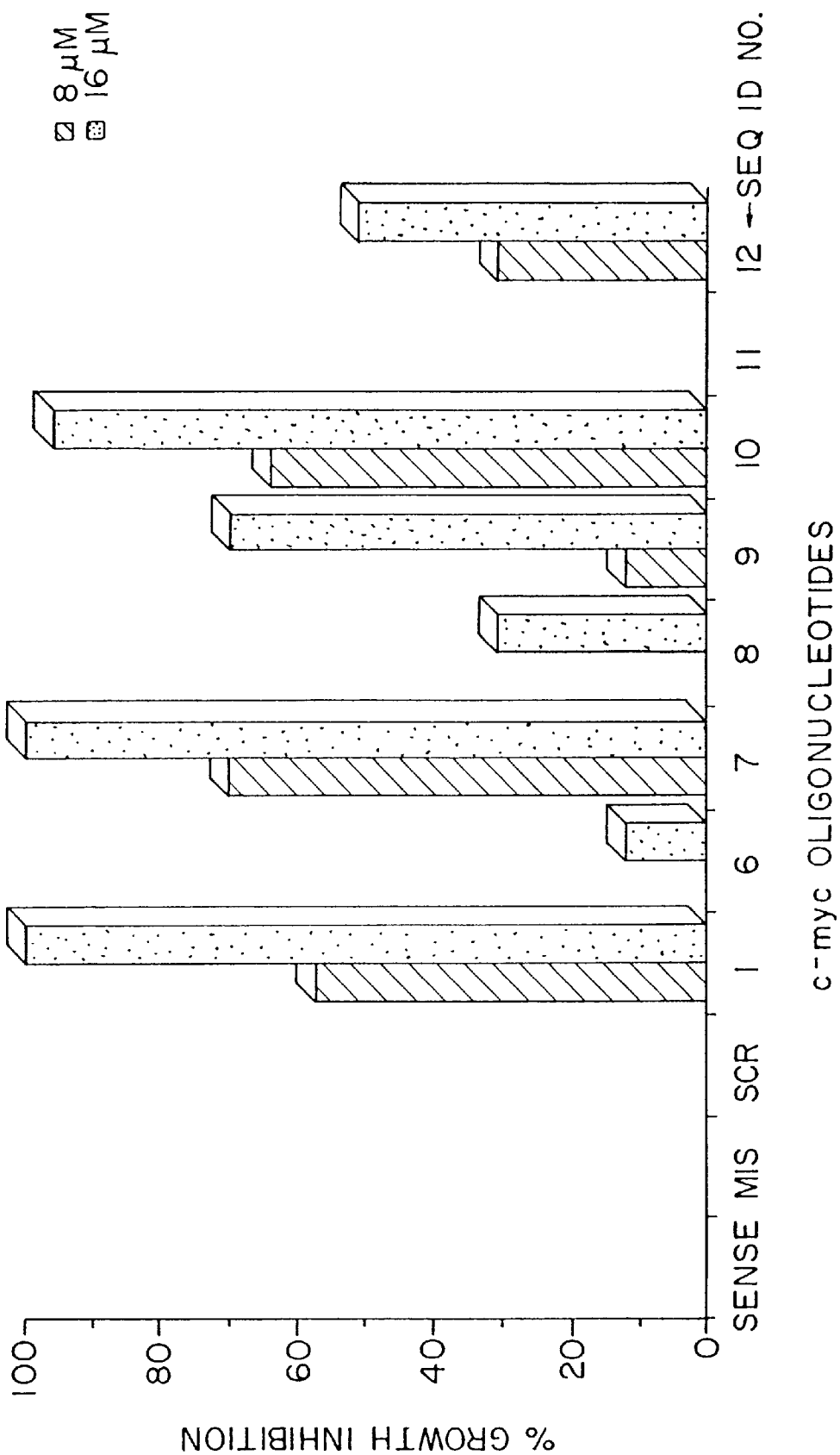
FIG. 12 is a schematic representation of the growth-inhibitory effect of various antisense sequences targeting c-myc mRNA in human SMCs. Percent inhibition at day 3 was assessed for antisense oligonucleotides SEQ ID NOS: 1 and 6–12 at 8 and 16 $\mu$M, and for sense, mismatched (mis), and scrambled sense (scr) oligonucleotides.

The results are set forth in FIG. 12. Various degrees of growth inhibition were obtained. The c-myc antisense oligonucleotides SEQ ID NOS: 7 and 10 provided a similar degree of growth inhibition in human SMCs compared with the translation initiation region-targeting oligomer, SEQ ID NO:1. Sense, mismatched (mis), and scrambled sense (scr) oligomers provided no growth inhibition. Results in FIG. 12 are expressed as the mean of three observations. The experiment was repeated twice. Similar results were obtained.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A method for inhibiting proliferation of smooth muscle cells in restenosis, comprising the step of:

locally administering to a vessel undergoing restenosis an effective amount of an antisense oligonucleotide specific for c-myc, by providing said oligonucleotide in a porous balloon catheter inserted into the lumen of the vessel.

2. The method according to claim 1 wherein the antisense oligonucleotide is complementary to a region of an mRNA encoding c-myc.

3. The method of claim 2 wherein said mRNA encoding c-myc has a translation initiation region and wherein said antisense oligonucleotide is complementary to the translation initiation region.

4. The method according to claim 3 wherein said antisense oligonucleotide has a length within the range of from 15 to 25 nucleotides.

5. The method of claim 4 wherein said effective amount is in the range of from 1 μg to 100 mg and wherein said step of locally administering includes delivering said effective amount to said site undergoing restenosis over a period in the range of from 30 seconds to 60 minutes.

6. A method according to claim 2 wherein the antisense oligonucleotide comprises at least one modified nucleotide.

7. A method according to claim 6 wherein the antisense oligonucleotide is a phosphorothioate antisense oligonucleotide.

8. The method according to claim 2 wherein said antisense oligonucleotide is selected from the group consisting of antisense oligonucleotides defined by SEQ ID NO:1, SEQ ID NO:7 and SEQ ID NO:10.

9. The method according to claim 8 wherein said antisense oligonucleotide is defined by SEQ ID NO:1.

10. A method for treating a patient suffering from restenosis comprising locally administering to a vessel undergoing restenosis an effective amount of an antisense oligonucleotide specific for c-myc, by providing said oligonucleotide in a porous balloon catheter inserted into the lumen of the vessel.

11. The method according to claim 10 wherein the antisense oligonucleotide is an oligonucleotide having a sequence capable of forming a stable duplex with a portion of an mRNA encoding c-myc.

12. The method according to claim 11 wherein the antisense oligonucleotide comprises at least one modified nucleotide.

\* \* \* \* \*

```
                        SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
             (A) LENGTH: 15
             (B) TYPE: nucleic acid
             (C) STRANDEDNESS: single
             (D) TOPOLOGY: linear (iv) ANTI-SENSE: yes (xi) SEQUENCE DESCRIPTION:  SEQ ID NO:1:

AACGTTGAGG GGCAT                                                    15

(2) INFORMATION FOR SEQ ID NO:2:

(i) SEQUENCE CHARACTERISTICS:
             (A) LENGTH: 15
             (B) TYPE: nucleic acid
             (C) STRANDEDNESS: single
             (D) TOPOLOGY: linear (iv) ANTI-SENSE: no (xi) SEQUENCE DESCRIPTION:  SEQ ID NO:2:

ATGCCCCTCA ACGTT                                                    15

(2) INFORMATION FOR SEQ ID NO:3:

(i) SEQUENCE CHARACTERISTICS:
             (A) LENGTH: 15
             (B) TYPE: nucleic acid
             (C) STRANDEDNESS: single
             (D) TOPOLOGY: linear (iv) ANTI-SENSE: no (xi) SEQUENCE DESCRIPTION:  SEQ ID NO:3:

TACGGGGTTG AGCAA                                                    15

(2) INFORMATION FOR SEQ ID NO:4:

(i) SEQUENCE CHARACTERISTICS:
             (A) LENGTH: 20
             (B) TYPE: nucleic acid
```

```
        (C) STRANDEDNESS: single
        (D) TOPOLOGY: linear (iv) ANTI-SENSE: no (xi) SEQUENCE DESCRIPTION: SEQ ID NO:4:

TGGTGCTCCA TGAGGAGACA                                          20

(2) INFORMATION FOR SEQ ID NO:5:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: no (xi) SEQUENCE DESCRIPTION: SEQ ID NO:5:

GTGTTTCAAC TGTTCTCGTC                                          20

(2) INFORMATION FOR SEQ ID NO:6:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:6:

AAAGTGCCCT CCCGCTGCTA                                          20

(2) INFORMATION FOR SEQ ID NO:7:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:7:

GGGAGAGTCG CGTCCTTGCT                                          20

(2) INFORMATION FOR SEQ ID NO:8:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO:8:

CCAGTGCAAA GTGCCCGCCC                                          20

(2) INFORMATION FOR SEQ ID NO:9:

(i) SEQUENCE CHARACTERISTICS:
        (A) LENGTH: 20
        (B) TYPE: nucleic acid
        (C) STRANDEDNESS: single
        (D) TOPOLOGY: linear (iv) ANTI-SENSE: yes
```

(xi) SEQUENCE DESCRIPTION: SEQ ID NO:9:

GGCCTTTTCA TTGTTTTCCA                                                          20

(2) INFORMATION FOR SEQ ID NO:10:

(i) SEQUENCE CHARACTERISTICS:
              (A) LENGTH: 20
              (B) TYPE: nucleic acid
              (C) STRANDEDNESS: single
              (D) TOPOLOGY: linear (iv) ANTI-SENSE: yes (xi) SEQUENCE DESCRIPTION: SEQ ID NO:10:

TCATGGAGCA CCAGGGGCTC                                                          20

(2) INFORMATION FOR SEQ ID NO:11:

(i) SEQUENCE CHARACTERISTICS:
              (A) LENGTH: 20
              (B) TYPE: nucleic acid
              (C) STRANDEDNESS: single
              (D) TOPOLOGY: linear (iv) ANTI-SENSE: yes (xi) SEQUENCE DESCRIPTION: SEQ ID NO:11:

CGGATCTCCC TTCCCAGGAC                                                          20

(2) INFORMATION FOR SEQ ID NO:12:

(i) SEQUENCE CHARACTERISTICS:
              (A) LENGTH: 20
              (B) TYPE: nucleic acid
              (C) STRANDEDNESS: single
              (D) TOPOLOGY: linear (iv) ANTI-SENSE: yes (xi) SEQUENCE DESCRIPTION: SEQ ID NO:12:

CGTTCTTTTT TCCCGCCAAG                                                          20

(2) INFORMATION FOR SEQ ID NO:13:

(i) SEQUENCE CHARACTERISTICS:
              (A) LENGTH: 15
              (B) TYPE: nucleic acid
              (C) STRANDEDNESS: single
              (D) TOPOLOGY: linear (iv) ANTI-SENSE: no (xi) SEQUENCE DESCRIPTION: SEQ ID NO:13:

AACGTGGATT GGCAG                                                               15

(2) INFORMATION FOR SEQ ID NO:14:

(i) SEQUENCE CHARACTERISTICS:
              (A) LENGTH: 15
              (B) TYPE: nucleic acid
              (C) STRANDEDNESS: single
              (D) TOPOLOGY: linear -continued

```
    (iv) ANTI-SENSE: no (xi) SEQUENCE DESCRIPTION: SEQ ID NO:14:

GAACGGAGAC GGTTT                                                  15
```